United States Patent
Tanabe et al.

(10) Patent No.: US 10,859,512 B2
(45) Date of Patent: Dec. 8, 2020

(54) X-RAY PHASE CONTRAST IMAGING APPARATUS

(71) Applicant: Shimadzu Corporation, Kyoto (JP)

(72) Inventors: Koichi Tanabe, Kyoto (JP); Toshinori Yoshimuta, Kyoto (JP); Kenji Kimura, Kyoto (JP); Hiroyuki Kishihara, Kyoto (JP); Yukihisa Wada, Kyoto (JP); Takuro Izumi, Kyoto (JP); Taro Shirai, Kyoto (JP); Takahiro Doki, Kyoto (JP); Satoshi Sano, Kyoto (JP); Akira Horiba, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 126 days.

(21) Appl. No.: 16/309,820

(22) PCT Filed: Mar. 15, 2017

(86) PCT No.: PCT/JP2017/010511
§ 371 (c)(1),
(2) Date: Dec. 13, 2018

(87) PCT Pub. No.: WO2017/217049
PCT Pub. Date: Dec. 21, 2017

(65) Prior Publication Data
US 2019/0175126 A1  Jun. 13, 2019

(30) Foreign Application Priority Data
Jun. 15, 2016  (JP) .................................. 2016-118933

(51) Int. Cl.
*G01N 23/041* (2018.01)
*A61B 6/00* (2006.01)
(Continued)

(52) U.S. Cl.
CPC ............. *G01N 23/041* (2018.02); *A61B 6/00* (2013.01); *A61B 6/4291* (2013.01); *G01N 23/046* (2013.01); *G01N 23/044* (2018.02)

(58) Field of Classification Search
CPC ...... A61B 6/4291; A61B 6/00; G01N 23/046; G01N 23/04
See application file for complete search history.

(56) References Cited

U.S. PATENT DOCUMENTS

| | | | |
|---|---|---|---|
| 2011/0243300 A1 | 10/2011 | Kaneko et al. | |
| 2012/0093297 A1* | 4/2012 | Kondoh | G01D 5/38 378/145 |

(Continued)

FOREIGN PATENT DOCUMENTS

| | | |
|---|---|---|
| JP | 2011-227041 A | 11/2011 |
| JP | 2012-20107 A | 2/2012 |

(Continued)

OTHER PUBLICATIONS

Notification of Reasons for Refusal dated Aug. 27, 2019, for corresponding Japanese Patent Application No. JP 2018-523320, submitted with a machine translation.

(Continued)

*Primary Examiner* — Blake C Riddick
(74) *Attorney, Agent, or Firm* — Muir Patent Law, PLLC

(57) ABSTRACT

Provided is a radiation imaging apparatus capable of performing precise imaging without performing pre-imaging in the absence of a subject. According to the present invention, it is possible to provide a radiation imaging apparatus capable of performing precise imaging without performing pre-imaging in the absence of a subject immediately before. That is, the apparatus of the present invention is provided with a phase grating 5 provided with a subject area and a reference area. Both areas each have a predetermined pattern that absorbs radiation, but the patterns are different from (Continued)

each other. In this area, an image of the phase grating 5 is observed in a moire pattern of a long period. This moire image of a long period changes in the positions due to the minute change in the relative position between the phase grating 5 and the absorption grating 6, so it becomes possible to detect the minute change of the relative position between the radiation source, the phase grating 5, and the absorption grating 6 from the image of the reference area.

11 Claims, 25 Drawing Sheets

(51) Int. Cl.
    *G01N 23/046*      (2018.01)
    *G01N 23/044*      (2018.01)

(56) References Cited

U.S. PATENT DOCUMENTS

| | | | |
|---|---|---|---|
| 2013/0032727 A1* | 2/2013 | Kondoh | G01N 23/046 250/394 |
| 2013/0070895 A1* | 3/2013 | Ouchi | G01N 23/041 378/62 |
| 2013/0077747 A1* | 3/2013 | Kamono | A61B 6/06 378/62 |
| 2013/0235973 A1 | 9/2013 | Murakoshi et al. | |
| 2014/0114615 A1* | 4/2014 | Nagai | G01N 23/20075 702/189 |
| 2014/0126690 A1 | 5/2014 | Yamaguchi | |
| 2014/0146939 A1* | 5/2014 | Zhang | G01T 1/2985 378/19 |
| 2014/0270060 A1* | 9/2014 | Date | A61B 6/484 378/36 |
| 2016/0252470 A1* | 9/2016 | Momose | G01N 23/20075 378/36 |

FOREIGN PATENT DOCUMENTS

| | | |
|---|---|---|
| JP | 2014-029314 A | 2/2014 |
| JP | 2014-90967 A | 5/2014 |
| WO | 2012/059724 A1 | 5/2012 |

OTHER PUBLICATIONS

International Search Report dated Apr. 25, 2017 for application No. PCT/JP2017/010511.
Written Opinion of the International Search Authority dated Apr. 25, 2017 for application No. PCT/JP2017/010511.

\* cited by examiner

Self-image generation processing

Ideal Transition of Image

Actual Transition of Image

X-RAY PHASE CONTRAST IMAGING APPARATUS

TECHNICAL FIELD

The present invention relates to a radiation imaging apparatus capable of imaging an internal structure of an object by utilizing radiation transmitted through the object.

BACKGROUND ART

Conventionally, various apparatuses have been conceived as a radiation imaging apparatus for imaging an internal structure of an object by making radiation transmit through the object. A commonly-used radiation imaging apparatus is configured to capture a radiation projection image by irradiating radiation to an object to make the radiation transmit through the object. In such a projection image, the contrasting density appears depending on the ease of permeation of radiation, which represents the internal structure of the object.

With such a radiation imaging apparatus, only objects having a property capable of absorbing radiation to some extent can be imaged. For example, soft biological tissues hardly absorb radiation. Even if it is tried to image such a tissue with a general device, nothing is reflected on the projection image. When trying to image the internal structure of an object that does not absorb radiation as described above, there is a theoretical limit in a general radiation imaging apparatus.

Under the circumstances, a radiation phase contrast imaging device that images an internal structure of an object by utilizing a phase contrast of transmitted radiation has been proposed. Such a device is configured to image an internal structure of an object using Talbot interference.

Talbot interference will be explained. From the radiation source 53 shown in FIG. 36, phase-aligned radiation is irradiated. When making the radiation transmit through a phase grating 55 which is in a streak form, the image of the phase grating 55 appears on the projection plane which is apart from the phase grating 55 by a predetermined distance (Talbot distance). This image is called a self-image. Note that this self-image is not just a projection image of the phase grating 55. The self-image occurs only at the position where the projection plane is separated from the phase grating 55 by the Talbot distance. The self-image is configured by the interference fringes caused by interference of light. The reason that the self-image of the phase grating 55 appears at the Talbot distance is that the phase of radiation generated from the radiation source 53 is aligned. When the phase of radiation is disturbed, the self-image appearing at the Talbot distance is also disturbed.

The radiation phase contrast imaging device is configured to image an internal structure of an object by utilizing the self-image disturbance. It is assumed that an object is placed between the radiation source and the phase grating 55. Since this object hardly absorbs radiation, most of the radiation incident on the object exits to the phase grating 55 side.

The radiation has not passed through the object completely as it is. The reason is that the phase of the radiation changes while passing through the object. The radiation exited the object passes through the phase grating 55 with the phase changed. The observation of the radiation on the projection plane arranged at the Talbot distance shows disturbances in the self-image of the phase grating 55. The degree of disturbances of this self-image represents the radiation phase change.

The specific magnitude of the phase change of the radiation transmitted the object changes depends on where the radiation passed through the object. If the object has a homogeneous configuration, the change of the radiation phase remains the same no matter where the radiation transmits through the object. In general, however, an object has some internal structure. When radiation is made to transmit such an object, the phase change does not remain the same.

Therefore, when the phase change is known, the internal structure of the object can be grasped. The phase change can be known by observing the self-image of the phase grating 55 at the Talbot distance. The detection of such a self-image is performed by a radiation detector. The radiation detector has a detection surface that detects radiation. By projecting a self-image on this detection surface, the radiation detector can perform imaging of the self-image (see, for example, Patent Document 1).

In order to grasp the internal structure of the object in detail, it is necessary to make the self-image finer as much. It is quite difficult to detect such a self-image with a radiation detector. Therefore, instead of capturing a self-image at once, an imaging method has been devised in which imaging is repeated several times to obtain a self-image. This method will be described concretely. In this method, an absorption grating having a pattern of a stripe shape is provided on the detection surface of the radiation detector. Since a self-image has a pattern of a stripe shape, a self-image and an absorption grating interfere with each other. A radiation detector can easily image the state of this interference.

When imaging is performed consecutively while changing the positional relationship between the self-image and the absorption grating, the state of interference changes according to the change of the positional relationship. Based on the plural interference images thus obtained, it is possible to grasp the original self-image. To change the positional relationship between the self-image and the absorption grating, it is realized by relatively moving the radiation source, the phase grating, and the absorption grating. There is a fringe scanning method as an indirect self-image capturing method.

Note that the method of imaging using the interference between the radiation beam of a stripe pattern and the absorption grating of a stripe pattern is not limited to the imaging related to the Talbot interference. Even in the case of imaging using edge illumination, it uses interference between the radiation beam of a stripe pattern and an absorption grating of a stripe pattern. Further, a method of directly detecting a self-image in the absence of an absorption grating has been proposed. Further, as described in Talbot interference, a method of imaging with a plurality of fan beams or pencil beams by replacing a phase grating with a mask grid has also been proposed.

PRIOR ART

Patent Document

Patent Document 1: International Patent Publication No. 2012/056724

SUMMARY OF THE INVENTION

Problems to be Solved by the Invention

However, the conventional radiation phase contrast imaging device has the following problems.

In other words, in a conventional radiation phase contrast imaging device, it is required to perform imaging in the absence of a subject for the purpose of grasping the In a conventional configuration, a self-image cannot be captured directly. Based on a plurality of interference images obtained by continuously performing image-capturing while changing the positional relationship between the self-image and the absorption grating, a self-image is reconstructed by computation. In the arithmetic processing for realizing this self-image reconstruction, the processing is executed on the premise that each of the interference images is captured when the self-image and the absorption grating become a predetermined positional relationship. It is possible to predict that each of the interference images will become what kind of images before image capturing. However, the actually obtained interference image is different from the predicted image since the subject is reflected. The difference from this prediction represents the internal structure of the subject.

The self-image and the absorption grating have fine stripe patterns. The capturing of the interference image must be performed when the self-image and the absorption grating are in specific positions. However, it is difficult to make the positional relationship between the self-image and the absorption grating ideal. When the grating position shifts due to the influence of the thermal expansion of the optical system, vibration, etc., or when the radiation generation point of the radiation source deviates slightly from the ideal position, the image capturing of the interference image is performed in a state in which the self-image and the absorption grating have a positional relationship deviated from the ideal positional relationship. In such a case, the arithmetic processing related to the reconstruction of the self-image is not operated properly, which in turn generates a self-image different from the actual.

Conventionally, in order to solve such a problem, a method has been conceived in which the positional relationship between the self-image and the absorption grating is actually measured. That is, first, in a state in which a subject is absent, interference images are continuously captured while changing the positional relationship between the phase grating and the absorption grating. Based on the obtained multiple interference images, the positional relationship between the self-image and the absorption grating is calculated. Then, in a state in which a subject is present, interference images are continuously captured while changing the positional relationship between the phase grating and the absorption grating. Finally, considering the calculated positional relationship, the interference image in which the subject appears is arithmetically processed to generate a phase image.

That is, according to a conventional configuration, before imaging a subject, imaging must be performed in the absence of a subject. It takes time and effort to perform the imaging. Such a problem becomes serious, especially when performing CT imaging. In the CT imaging, tomographic images of an internal structure of a subject are captured by repeatedly capturing the self-image while rotating the subject. In such an imaging method, the number of the interference images becomes considerably large, and therefore it takes time for the imaging. So, the positional relationship of the grating changes during the imaging. For this reason, even if the continuous imaging in the absence of a subject is performed and then the positional relationship of the gratings is calculated before CT imaging, it could happen that the self-image obtained at the end of the imaging is far apart from the self-image of the calculated grating position.

Such disadvantages do not occur only in the imaging method using Talbot interference. A similar problem may arise even in the imaging using edge illumination or a method of directly detecting a self-image.

The present invention has been made in view of the aforementioned circumstances, and an object of the present invention is to provide a radiation imaging apparatus capable of performing precise imaging without performing pre-imaging in the absence of a subject immediately before.

Means for Solving the Problems

In order to solve the aforementioned problems, the present invention has the following configuration.

That is, the radiation imaging method according to the present invention includes:

a radiation source configured to irradiate radiation;

a grating provided with a subject grating area which is an area provided with a predetermined pattern for absorbing the radiation and through which a radiation beam that passes through the subject passes and a reference grating area which is an area provided with a pattern different from the pattern of the subject grating area;

(A) an absorption grating provided with a predetermined pattern for absorbing the radiation;

(B) a detection unit configured to detect an image of the grating on a detection surface in which detection elements for detecting the radiation are arranged in a matrix;

(C1) a position unitcalculator configured to calculate a relative position of the radiation source, the grating, and the absorption grating by detecting moire occurring between an image of the pattern of the reference grating area appearing on the detection surface and a pattern on the absorption grating; and an image generation unit configured to execute a correction by referring to the calculated relative position when generating an image based on an output of the detection unit.

[Functions and Effects] According to the present invention, it is possible to provide a radiation imaging apparatus capable of performing precise imaging without performing pre-imaging in the absence of a subject immediately before. That is, the apparatus of the present invention is provided with a grating provided with a subject area and a reference area. Both areas each have a predetermined pattern that absorbs radiation, but the patterns are different from each other. The image of the grating (grating image) focused on the detection surface is captured with a detection element provided so as to cover the detection surface. By making the pitch at which the pattern of the subject area repeats the integer multiple of the pitch at which the pattern in the absorption grating repeats, the image of the grating can be observed at the integer multiple pixel period.

However, the change in the relative position between the grating and the detection surface which is equal to or less than the pitch/integer multiple of the detection element is more difficult to detect than in the subject area image. Especially in cases where the integer multiple is about 2 to 8, the change in the relative position which is difficult to detect becomes a large error factor. According to the present invention, a reference area having a pattern different from that of the subject area is provided. In this area, an image of the grating is observed in a moire pattern of a long period. The position of this moire-like image of a long period is changed by the minute change of the relative position between the grating and the detection surface, so it is possible to detect minute changes of the relative position of the radiation source, the grating, and the detection surface from the image of the reference area. Even if the subject appears in the reference area, it is possible to detect the change in the relative position by averaging the direction in which the grating absorption extends, but it is preferable that there is no subject in the reference area.

Further, the same effects can be obtained by providing the reference areas having a different pitch in the detection surface, instead of providing a reference area to the grating.

It is not necessary to provide an absorber in the subject area portion. In this case, the relative position among the radiation source, the grating, and the detection surface can be accurately known. By correcting it, it becomes possible to improve the imaging spatial resolution of the subject arranged near the grating.

Further, in the radiation imaging apparatus according to the present invention includes:

a radiation source configured to irradiate radiation;

a grating provided with a subject grating area which is an area provided with a predetermined pattern for absorbing the radiation and through which a radiation beam that passes through the subject passes and a reference grating area which is an area provided with a pattern different from the pattern of the subject grating area;

(B) a detection unit configured to detect an image of the grating on a detection surface in which detection elements for detecting the radiation are arranged in a matrix;

(C2) a position calculation unit configured to calculate a relative position of the radiation source and the grating by detecting moire occurring between an image of the pattern of the reference grating area appearing on the detection surface and an array of each detection element; and an image generation unit configured to execute a correction by referring to the calculated relative position when generating an image based on an output of the detection unit.

[Functions and Effects] The present invention can also be applied to a configuration having no absorption grating. That is, in the present invention, the moire generated between the image of the pattern of the reference area appearing on the detection surface and the array of each detection element can be used to find the relative position between the grating and the detection surface.

Further, in the above-described radiation imaging apparatus, it is preferable that the reference area of the grating be provided at an end portion of the subject area in one direction.

[Functions and Effects] According to the above-described configuration, since the reference area is provided at the end portion, the reference area does not obstruct the imaging of the subject.

Further, in the above-described radiation imaging apparatus, it is more preferable that the reference area of the grating be provided at both end portions of the subject area in one direction.

[Functions and Effects] According to the above-described configuration, the positional displacement of the grating in the rotational direction can also be detected by providing the reference area at both ends.

Further, in the above-described radiation imaging apparatus, it is more preferable that the pattern in the reference area be configured by arranging dark lines for absorbing radiation, the pattern in the absorption grating be configured by arranging dark lines for absorbing radiation, and an array pitch of the dark lines in the reference area be not an integer multiple of an array pitch of the dark lines in the absorption grating.

Further, in the above-described radiation imaging apparatus, it is more preferable that a pattern in the reference area be configured by arranging dark lines for absorbing radiation, and an array pitch of the dark lines be not an integer multiple of an array pitch of the detection element.

[Functions and Effects] According to the above-described configuration, a moire can be assuredly generated.

Further, in the above-described radiation imaging apparatus, it is more preferable that the pattern in the subject area of the grating be for a moire single imaging method.

[Functions and Effects] The present invention can also be applied to imaging using a moire single imaging method.

Further, in the above-described radiation imaging apparatus, it is more preferable that a plurality of images be added based on the relative position calculated by the position calculation unit.

[Functions and Effects] According to the above-described configuration, it is possible to perform imaging while considering the temporal change in the misalignment between the grating and the absorption grating or in the misalignment between the grating and the detection surface while capturing a plurality of images.

In addition, this specification also discloses the following invention.

(1) In the above-described radiation imaging apparatus, it is more preferable that the detection element for detecting the radiation be configured by arranging a detection area for detecting radiation and a non-detection area which allows transmission of radiation.

[Functions and Effects] The present invention can be used in an apparatus related to an edge illumination method as described above. In that case, by setting the detection area for detecting radiation in the detection element and the non-detection area which allows transmission of radiation and making the pitch of the grating image the same as the pitch of the detection area for detecting radiation, the edge of the grating image can be detected.

(2) Further, in the above-described radiation imaging apparatus, it is more preferable to configure such that a detection element for detecting radiation is further overlapped in addition to the detection element for detecting radiation.

[Functions and Effects] In the present invention, in the case of using the edge illumination method described above, by also detecting the radiation that transmitted the radiation transmission portion in the detection element, it becomes possible to improve the detection sensitivity and detect more accurate phase image and dark field image.

(3) Further, in the above-described radiation imaging apparatus, it is possible to further provide a secondary grating in which a grating absorber which absorbs radiation and extends in one direction is arranged in a direction orthogonal to the one direction between the grating and the detection element which detects radiation.

[Functions and Effects] The present invention can be applied to an apparatus utilizing the principle of acquiring a phase or a dark field image from moire caused by the grating or an edge illumination method using two gratings. Further, the same effects can be obtained by providing a reference area different in pitch in the secondary grating instead of providing a reference area in the grating.

(4) In the above-described radiation imaging apparatus, it is more desirable to configure such that the phase image or the dark field image is calculated from a plurality of captured images obtained by changing the relative position of the radiation source, the grating, the secondary grating, and the detection unit.

[Functions and Effects] The present invention can be used for a phase image or dark field imaging apparatus utilizing a fringe scanning method.

(5) In the above-described radiation imaging apparatus, it may be configured such that the grating image reflected on the detection surface is a self-image of the grating occurring by Talbot interference.

[Functions and Effects] In the present invention, it is possible to improve the detection sensitivity of the phase/dark field image by making the grating pitch small enough to cause Talbot interference.

(6) Further, in the above-described radiation imaging apparatus, it is also possible to configure such that a third grating is added between the radiation source and the grating.

[Functions and Effects] In the present invention, it is also possible to configure a device having a Talbot-Lau configuration by adding a multi-slit.

(7) Further, in the above-described radiation imaging apparatus, it is more desirable to perform tomosynthesis imaging or CT imaging.

[Functions and Effects] According to the present invention, by adapting to tomosynthesis imaging or CT imaging which requires plural imaging for a long time, it is possible to accurately correct the relative position which changes between imaging.

Effects of the Invention

According to the present invention, it is possible to provide a radiation imaging apparatus capable of performing precise imaging without performing pre-imaging in the absence of a subject immediately before. That is, the apparatus of the present invention is provided with a grating provided with a subject area and a reference area. Both areas each have a predetermined pattern that absorbs radiation, but both the patterns are different from each other. In this area, the image of the grating is observed in a moire pattern of a long period. The position of the moire-like image of this long period changes by the minute change of the relative position between the grating and the detection surface, so it becomes possible to detect minute changes of the relative position of the radiation source, the grating, and the detection surface from the image of the reference area.

EMBODIMENTS FOR CARRYING OUT THE INVENTION

Hereinafter, the best mode for carrying out the invention will be described. X-rays correspond to the radiation of the present invention. An FPD is an abbreviation of a flat panel detector. In the FPD of Example 1, an image of a phase grating which appears on a detection surface where X-rays are incident is a self-image of the phase grating caused by Talbot interference.

EXAMPLE 1

Figure 1:
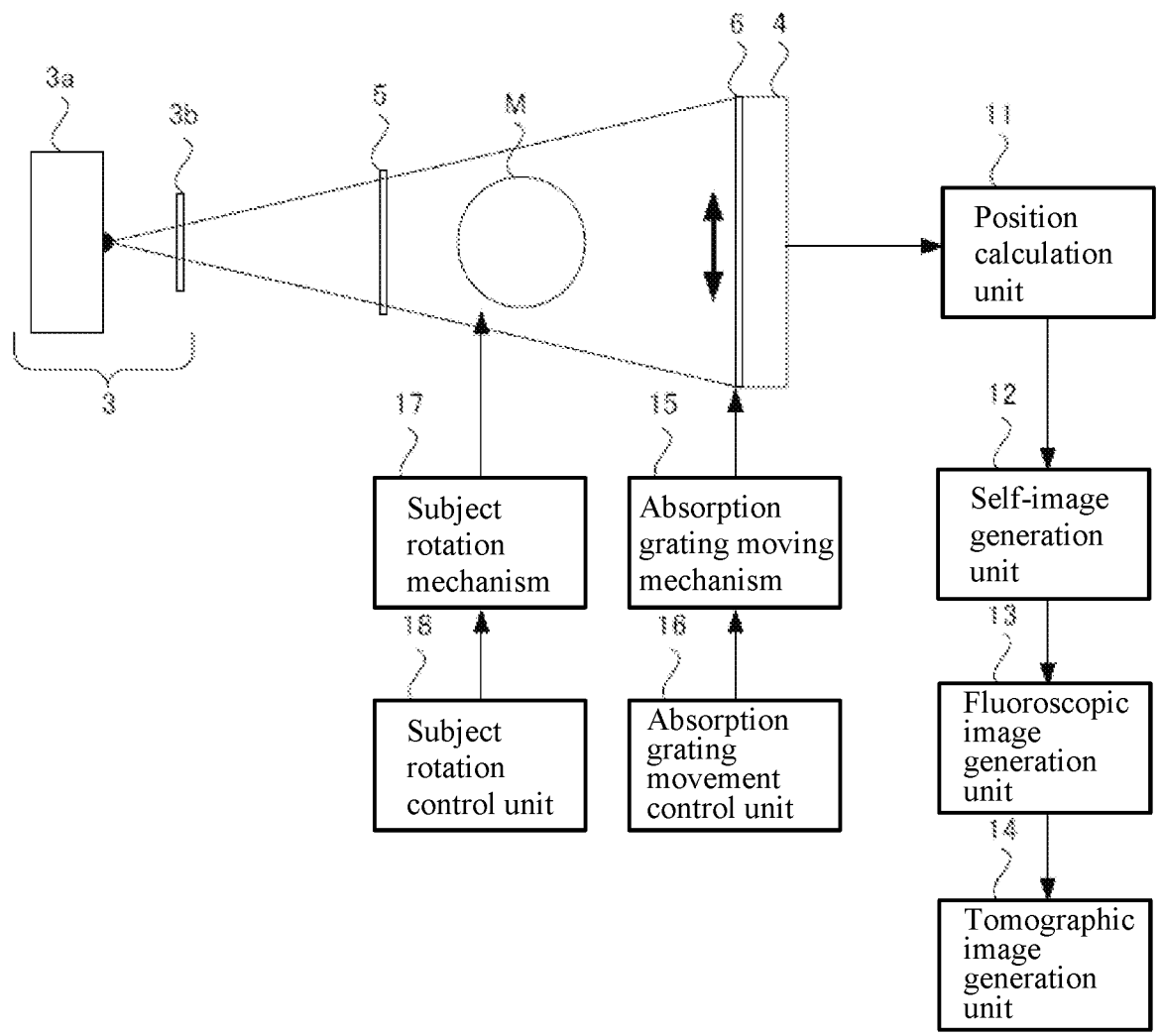
FIG. 1 is a functional block diagram explaining an overall structure of a radiation imaging apparatus according to Example 1.
Figure 36:
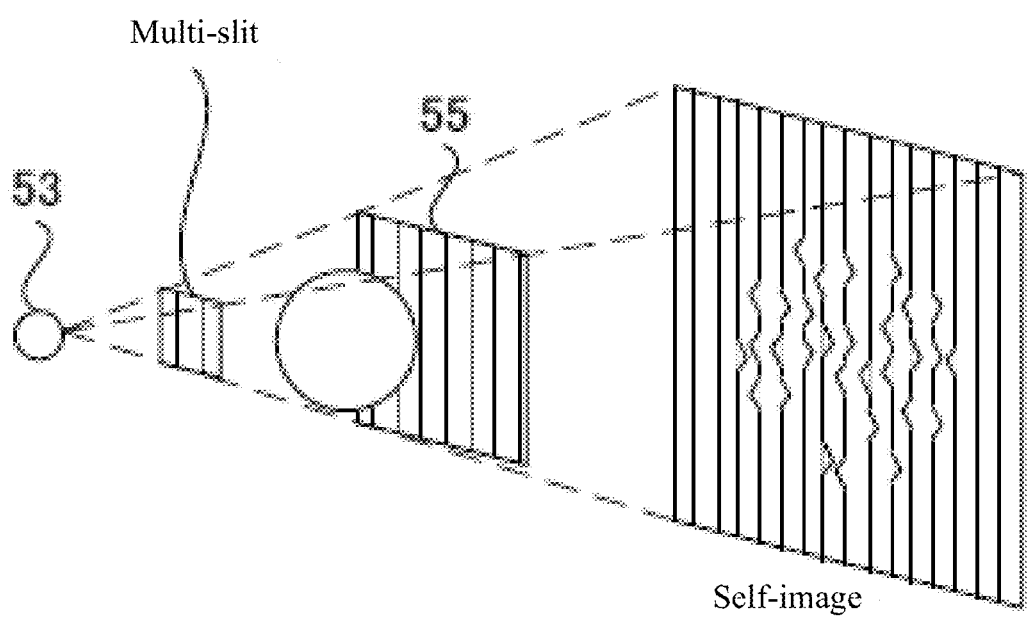
FIG. 36 is a diagram explaining a configuration of a radiation imaging apparatus according to a conventional configuration.

FIG. 1 is a functional block diagram illustrating the configuration of an X-ray phase contrast imaging apparatus according to the present invention. As shown in FIG. 1, the X-ray source 3 according to the present invention is provided with a positive electrode 3a on which electrons collide and a multi-slit 3b on which X-rays irradiated from the positive electrode 3a are incident, and is configured to irradiate X-rays. The positive electrode 3a is a target of electrons, and X-rays are generated when a fast electron collides against the positive electrode. X-rays are generated at a single focal point. The X-ray source 3 irradiates X-rays. The X-ray source 3 is configured to output X-rays having a specific wavelength. A subject M is placed between the phase grating 5 and the FPD 4. Note that, as shown in FIG. 36, it may be configured such that the subject M is placed between the multi-slit 3b and the phase grating 5. Note that the X-ray source 3 corresponds to the radiation source of the present invention. The FPD 4 corresponds to the detection unit of the present invention, and the phase grating 5 corresponds to the grating of the present invention.

The fan-shaped X-ray beam emitted from the positive electrode 3a is incident on the multi-slit 3b. The multi-slit 3b is made of a material, such as, e.g., gold, which is easy to be processed, and has a thickness to the extent that X-rays are not transmitted. The multi-slit 3b is configured such that slits extending in the vertical direction are arranged in the lateral direction. Each of the slits is a through-hole of the multi-slit 3b. In the multi-slit 3b, slits that allow transmission of radiation generated at a single generation point are arranged at a constant pitch in a direction orthogonal to the extending direction of the slit, and X-rays incident on portions where no slits S are provided are absorbed.

The X-ray beam generated at the positive electrode 3a passes through one of the slits provided in the multi-slit 3b and exits from the multi-slit 3b. At this time, each of the X-ray beams that have passed through the slits of the multi-slit 3b interferes, turns into an X-ray beam with high coherency, and goes toward the phase grating 5 (see FIG. 1).

Figure 2:
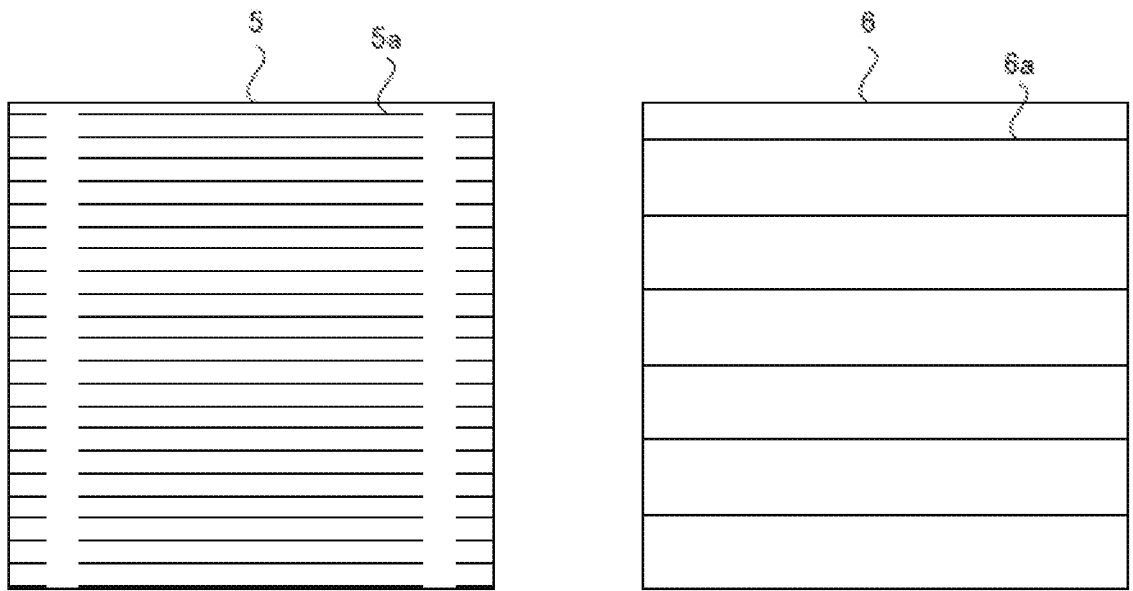
FIG. 2 is a plan view explaining a phase grating and an absorption grating according to Example 1.

The left side of FIG. 2 shows the phase grating 5. The phase grating 5 has a plurality of absorption lines 5a which absorb X-rays and extend in a linear shape. The absorption lines 5a are arranged in a vertical direction at a predetermined pitch in a direction perpendicular to the extending direction (lateral direction). The X-ray beam emitted from the multi-slit 3b passes through the phase grating 5. At that time, a part of the X-ray beam is absorbed by the phase grating 5. The X-ray beam emitted from the phase grating 5 has a pattern in which a plurality of bright lines remained without being absorbed by the absorption lines 5a is reflected. Since the pitch of the absorption line 5a of the phase grating 5 is sufficiently small, interference occurs between bright lines. Due to this interference, a streak form-like image similar to the image of the phase grating 5 appears at a distance away from the phase grating 5 by the Talbot distance. It should be noted that that this image is not just a shadow of the phase grating 5 but an interference fringe caused by interference. This image is called a self-image. The X-rays emitted from the phase grating 5 are directed to the FPD 4 (see FIG. 1). The FPD 4 is configured to detect a self-image of the phase grating 5 caused by the Talbot interference at a detection surface 4a for detecting X-rays.

The FPD 4 is, for example, a direct conversion type X-ray detector. That is, the FPD 4 has a conversion layer for converting X-rays into an electron/hole pair (charge carrier pair). The carriers generated in the conversion layer are captured by and accumulated in each of the detection elements 4p. When a signal for outputting a carrier is sent to the detection element 4p, the detection element 4p outputs the accumulated carriers as a detection signal. The fineness of this detection element 4p is a main factor determining the spatial resolution of the FPD 4. The smaller the detection element 4p, the better the spatial resolution of the FPD 4, so that it is possible to detect a finer structure. The conversion layer corresponds to the conversion portion of the present invention. Instead of this configuration, the FPD 4 according to Example 1 may be configured to detect fluorescence caused by X-rays. The FPD 4 has a configuration in which the image of the phase grating 5 is projected onto the detection surface 4a in which detection elements 4p for detecting X-rays are arranged in a matrix and the image of the phase grating 5 is detected.

The absorption grating 6 is provided so as to cover the detection surface 4a on the FPD 4. The absorption grating 6 has a plurality of absorption lines 6a which absorb X-rays and extend in a linear shape. The absorption lines 6a are arranged at a predetermined pitch in a direction perpendicular to the extending direction. The pattern of this absorption line 6a of the stripe pattern and the pattern of the phase grating 5 of the stripe pattern interfere with each other. The state of this interference is detected by the FPD 4. In the absorption grating 6, an elongated absorption line 6a which absorbs X-rays is arranged in a direction orthogonal to the direction in which the absorption line 6a extends. The extending direction of the absorption line 6a of the absorption grating 6 matches the extending direction of the absorption line 5a of the phase grating 5. Note that the absorption grating 6 corresponds to the secondary grating of the present invention. The absorption grating 6 is provided with a predetermined repetitive pattern for absorbing X-rays.

Figure 3:
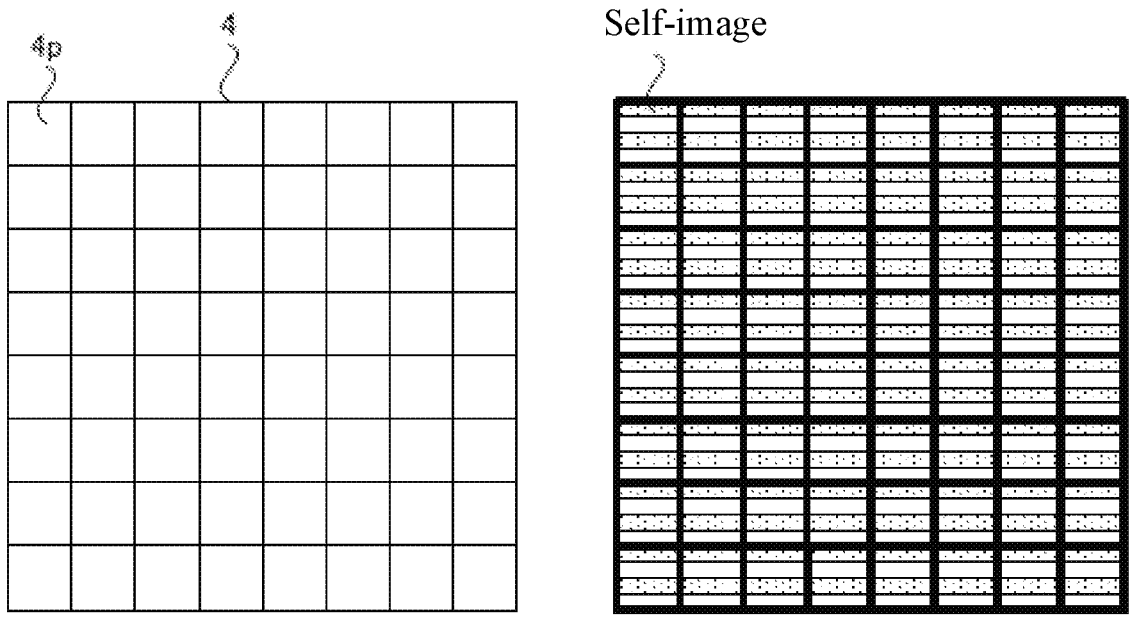
FIG. 3 is a plan view explaining a radiation detection surface and how a self-image is reflected on the detection surface according to Example 1.

The left side of FIG. 3 explains the configuration of the X-ray detection surface 4a of the FPD 4. The detection surface 4a of the FPD 4 has such a shape that the rectangular self-image of the phase grating 5 is reflected thereon. Therefore, the detection surface 4a of the FPD 4 has a rectangular structure like the phase grating 5. On the detection surface 4a of the FPD 4, rectangular detection elements 4p are arranged in a matrix. The extending direction of the absorption line 5a of the phase grating 5 coincides with the horizontal direction which is the direction in which the detection elements 4p in the detection surface 4a of the FPD 4 are arranged. The array direction of the absorption lines 5a of the phase grating 5 coincides with the vertical direction of the detection surface 4a of the FPD 4. In the phase grating 5, absorption lines which absorb X-rays and extend in one direction are arranged in a direction orthogonal to the one direction. The vertical direction of the array of detection elements 4p coincides with the array direction of absorption lines 6a of the absorption grating 6. The lateral direction of the array of the detection elements 4p coincides with the extending direction of the absorption line 6a of the absorption grating 6.

The right side of FIG. 3 shows how the self-image of the phase grating 5 is reflected on the detection surface 4a. On the right side of FIG. 3, the detection element 4p on the detection surface 4a is depicted and emphasized with thick lines. As can be seen from the figure, two dark lines constituting the self-image are reflected on a single detection element 4p. This configuration is for convenience of explanation. Actually, four dark lines constituting a self-image are reflected on a single detection element 4p. In this way, the array pitch of the detection elements 4p in the vertical direction is an integer multiple of the array pitch of the dark lines of the self-image of the phase grating 5 appearing on the detection surface 4a. At this time, it is important to note that the array pitch of the detection elements 4p is not necessarily an integer multiple of the array pitch of the absorption lines 5a of the phase grating 5. The self-image of the phase grating 5 is larger than the phase grating 5. Since X-rays spread radially from the X-ray source 3, the image of the phase grating 5 is enlarged and reflected on the detection surface 4a. The array pitch of the absorption line 5a of the phase grating 5 is set to be an integer multiple of the array pitch of the dark lines of the self-image of the phase grating 5 appearing on the detection surface 4a.

As described above, in the device according to Example 1, the self-image has a finer structure than the structure that can be grasped by the detection element 4p. Therefore, it should be inherently impossible to capture the self-image in this FPD 4. However, it is possible to capture the self-image by repeating the imaging many times. This point will be described later.

The self-image according to the present invention has a characteristic configuration at the right end and the left end. However, on the right side of FIG. 3, this characteristic configuration is omitted for convenience of explanation. The structure at both ends of the self-image will also be described later.

Figure 4:
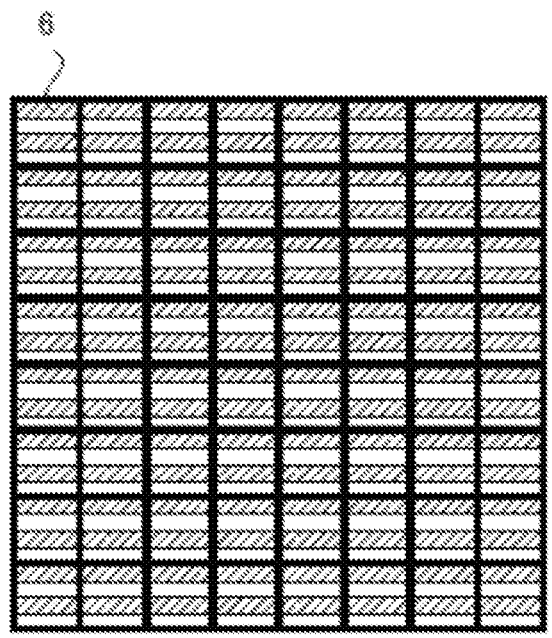
FIG. 4 is a plan view explaining how the absorption grating according to Example 1 covers the detection surface.

FIG. 4 shows the state in which the detection surface 4a is covered with the absorption grating 6. In FIG. 4, the detection element 4p on the detection surface 4a is highlighted with thick lines. As can be seen from the figure, two absorption lines 6a of the absorption grating 6 are reflected on a single detection element 4p. This configuration is for convenience of explanation. Actually, four absorption lines 6a are reflected on a single detection element 4p. That is, the array pitch of the detection element 4p in the vertical direction is an integer multiple of the array pitch of the absorption lines 6a. Further, in the device according to Example 1, the array pitch of the self-image appearing on the detection surface 4a and the array pitch of the absorption line 6a constituting the absorption grating 6 are the same.

<Absorption Grating Moving Mechanism>

The absorption grating moving mechanism 15 explained in FIG. 1 will be described. The absorption grating moving mechanism 15 is configured to move the absorption grating 6 in the array direction of the absorption lines 6a (vertical direction: the direction orthogonal to the direction in which the absorption line 6a extends) with respect to the detection surface 4a. The absorption grating movement control unit 16 is provided for the purpose of controlling the absorption grating moving mechanism 15. The absorption grating moving mechanism 15 is configured to change the positional relationship between the image of the phase grating 5 appearing on the detection surface and the absorption grating 6 in a direction orthogonal to one direction. This absorption grating moving mechanism 15 is provided for the purpose of changing the relative position between the absorption grating 6 and the self-image of the phase grating 5. Therefore, the absorption grating moving mechanism 15 and the absorption grating movement control unit 16 are specific means for changing the relative position between the absorption grating 6 and the self-image of the phase grating 5. The absorption grating moving mechanism 15 corresponds to the relative position changing unit of the present invention.

Even by the configuration in which the absorption grating moving mechanism 15 and the absorption grating movement control unit 16 are not provided, the relative position can be changed. For example, the relative position can be changed by moving the positive electrode 3a in the array direction (vertical direction) of the absorption lines 6a, and the relative position can also be changed by moving the multi-slit 3b in the array direction (vertical direction) of the absorption lines 6a. Further, by moving the phase grating 5 in the array direction of the absorption lines 6a, the relative position can be changed. In these cases, a moving mechanism (source moving mechanism, multi-slit moving mechanism, phase grating moving mechanism) for moving each part to be moved is provided instead of the absorption grating moving mechanism 15. In these cases, a control unit (light source movement control unit, multi-slit movement control unit, phase grating movement control unit) that controls the moving mechanism is provided instead of the absorption grating movement control unit 16. As the following description of Example 1, the configuration for moving the absorption grating 6 will be described.

Figure 5:
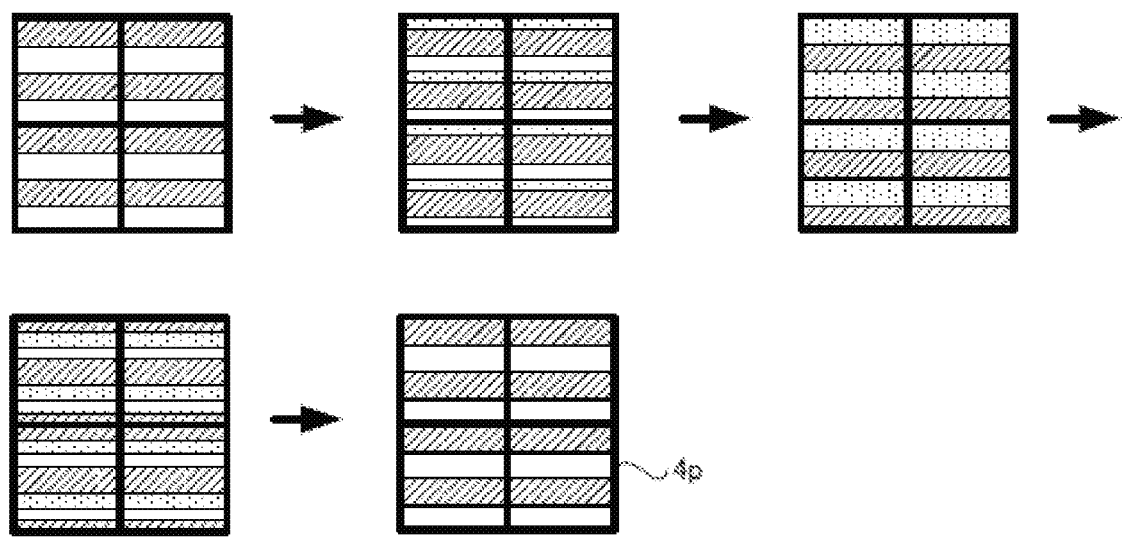
FIG. 5 is a plan view explaining how the absorption grating according to Example 1 moves with respect to the detection surface.

FIG. 5 shows how the absorption grating 6 is moved by the absorption grating moving mechanism 15. FIG. 5 shows one range in which the detection elements 4p are arranged in the vertical 2×horizontal 2 on the detection surface. Therefore, there are four absorption lines 6a of the absorption grating 6 in this range. In the state on the left side of the upper row of FIG. 5, the absorption line 6a and the dark lines constituting the self-image of the phase grating 5 are just overlapped. In this state, the X-rays can pass through the gap between the adjacent absorption lines 6a.

From this state, when the absorption grating 6 is moved in the array direction (vertical direction) of the absorption lines 6a, the absorption grating 6 moves relative to the self-image of the phase grating 5. Then, the dark line of the self-image of the phase grating 5 appears so as to fill the gap between adjacent absorption lines 6a. As a result, on the detection element 4p, the area of the dark area where X-rays do not hit will increase. As the absorption grating 6 is further moved, the dark lines of the self-image of the phase grating 5 cover the gap between the adjacent absorption lines 6a this time. Then, X-rays reaching the detection element 4p becomes extremely small.

When moving the absorption grating 6 from this state, this time, the dark line of the self-image starts overlapping the absorption line 6a again. As a result, on the detection element 4p, the area of the dark area where X-rays do not hit will decrease. When further moving the absorption grating 6 afterwards, the absorption line 6a and the dark line constituting the self-image of the phase grating 5 return to the state in which the dark line just overlaps the absorption line.

Figure 6:
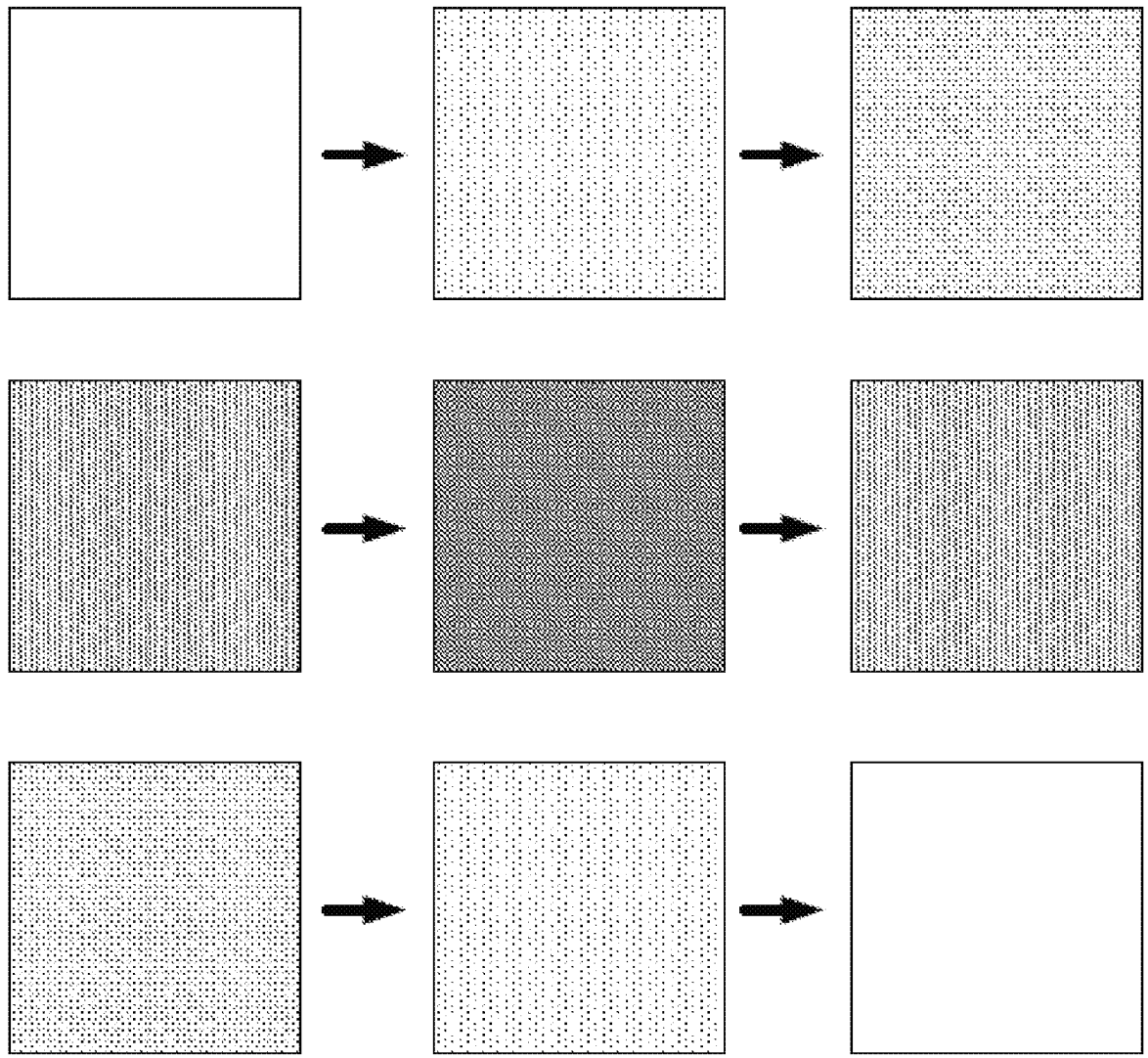
FIG. 6 is a schematic diagram explaining images continuously captured while moving the absorption grating according to Example 1 with respect to an FPD.

FIG. 6 shows an interference image (interference image) obtained by capturing how the self-image of the phase grating 5 and the absorption grating 6 interfere while moving the absorption grating 6 in the array direction of the absorption lines 6a. The array pitch of the absorption lines 6a constituting the absorption grating 6 and the array pitch of the dark lines constituting the self-image of the phase grating 5 are the same, and it is configured such that when integer multiplying the array pitch, it becomes the array pitch of the detection elements 4p. Therefore, no moire occurs between the phase grating 5 and the array of the detection elements 4p, and no moire occurs between the absorption grating 6 and the array of detection elements 4p. Therefore, no interference fringe appears in any interference image.

As the interference image is continuously captured while moving the absorption grating 6, a bright interference image is acquired at the beginning of the continuous imaging. Eventually, the resulting interference image gets darker gradually, after the darkest, it gradually gets brighter and returns to its original brightness. Such a change in the brightness of the interference image is caused by the relative movement between the absorption grating 6 and the self-image of the phase grating 5 described with reference to FIG. 5.

Such movement of the absorption grating 6 is realized by the absorption grating moving mechanism 15. The absorption grating moving mechanism 15 moves the absorption grating 6 by at least the array pitch of the absorption lines 6a of the absorption grating 6. The continuous imaging of the interference image is executed during that time. The number of interference images to be captured is, for example, eight (8). As shown in FIG. 6, nine (9) interference images may be captured.

<Self-Image Generation Portion>

Figure 7:
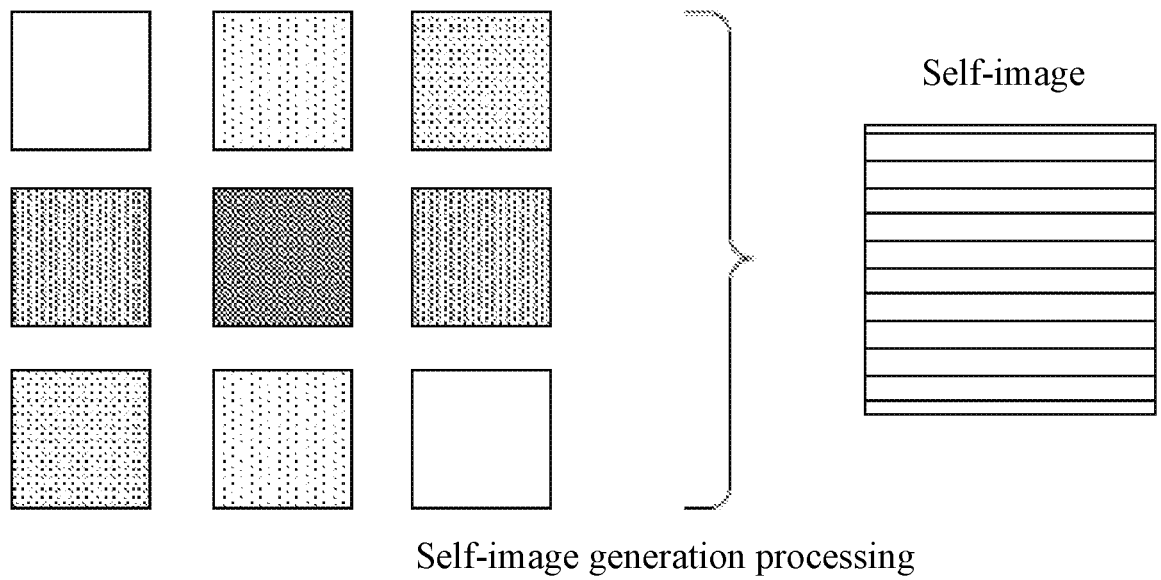
FIG. 7 is a schematic diagram explaining self-image generation processing according to Example 1.

A series of interference images are sent to the self-image generation unit 12. In the self-image generation unit 12, as shown in FIG. 7, it is configured such that the original self-image is calculated based on a series of interference images continuously captured while changing the relative position between the absorption grating 6 and the self-image of the phase grating 5. Since the self-image generation unit 12 of the present invention is configured to accurately reproduce the self-image taking into account the degree to which the relative position between the absorption grating 6 and the self-image of the phase grating 5 is deviated from the ideal, the point will be explained. The self-image generation unit 12 corresponds to the grating image generation unit of the present invention.

Figure 8:
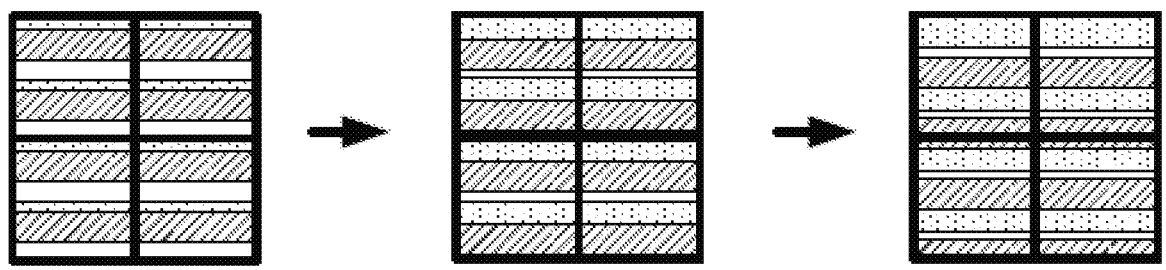
FIG. 8 is a schematic diagram explaining the positional displacement between the absorption grating and the detection surface according to Example 1.
Figure 8:
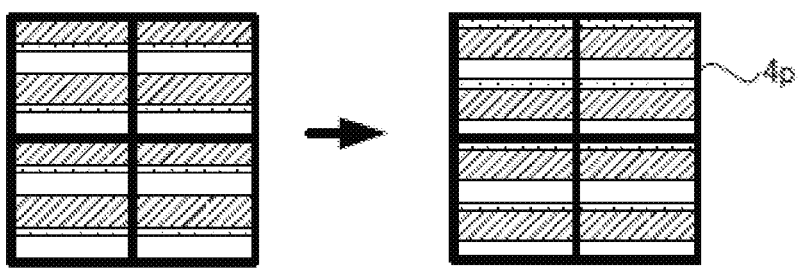

FIG. 8 shows the change of the relative position between the absorption grating 6 and the self-image of the phase grating 5 related to the actual interference image continuous imaging. Compared with the ideal relative movement shown in FIG. 5, the imaging start state is different. That is, ideally, at the start of imaging in a state in which the absorption line 6a of the absorption grating 6 is overlapped with the self-image of the phase grating 5. But, actually, the positioning of the absorption grating 6 and the self-image of the phase grating 5 is not sufficient, so the imaging is started in a state in which they are displaced from each other. It is assumed that the continuous imaging is performed while moving the absorption grating 6 from this state. In this case, the absorption grating 6 moves at the same speed as in the ideal case described with reference to FIG. 5, so that the initial displacement will not be eliminated. As a result, the relative position does not become ideal in all interference images.

The self-image generation unit 12 cannot accurately generate the original self-image based on the interference image which could not perform continuous imaging as ideal as described above. The self-image reflected on the detection surface 4a is disturbed under the influence of the subject M. When capturing an interference image including this disturbance, if it is assumed that the influence of the positional deviation between the absorption grating 6 and the self-image of the phase grating 5 is included in the interference image in the disturbance, it becomes considerably difficult to grasp the original self-image.

Figure 9:
FIG. 9 is a schematic diagram explaining the transition of the continuously captured images according to Example 1.
Figure 9:
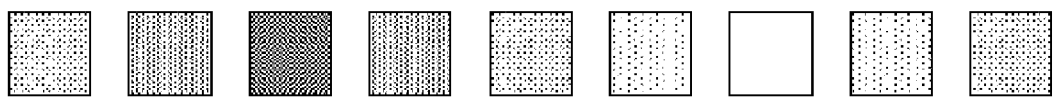

The positional deviation between the absorption grating 6 and the self-image of the phase grating 5 can be grasped by continuously capturing the interference image while moving the absorption grating 6. FIG. 9 explains the circumstances. The upper row of FIG. 9 shows an ideal transition of an interference image obtained when performing continuous imaging while moving the absorption grating 6. On the other hand, the lower row of FIG. 9 shows an interference image obtained when performing continuous imaging while actually moving the absorption grating 6. When comparing the upper row and the lower row of FIG. 9, it can be found that the timings at which the darkest interference image appears differ from each other. This difference in timing indicates how much the absorption grating 6 and the self-image of the phase grating 5 deviates from the ideal.

Therefore, by calculating how much degree the absorption grating 6 and the self-image of the phase grating 5 deviate from the ideal based on the consecutively captured interference image while moving the absorption grating 6, it seems that it is possible to retrieve only the information on the pattern of the self-image from a series of interference images in which the influence of the positional deviation of the absorption grating 6 and the self-image of the phase grating 5 is superimposed on the pattern of the self-image. However, it is not so easy in practice. That is, this is because not only the positional deviation between the absorption grating 6 and the self-image of the phase grating 5 but also the influence of the pattern of the self-image disturbed by the influence of the subject M are also superimposed in the interference images continuously imaged while moving the absorption grating 6.

Under the circumstances, according to a conventional configuration, first, interference images are continuously captured while moving the absorption grating 6 in the absence of the subject M. Then, based on this series of interference images, the positional deviation between the absorption grating 6 and the self-image of the phase grating 5 is calculated. As described above, by measuring the positional deviation in advance, based on a series of interference images captured in a state in which the subject M is reflected, it is possible to accurately acquire the self-image disturbed by the influence of the subject M.

<Most Characteristic Configuration of Present Invention>

According to the present invention, even without performing the image capturing in the absence of the subject M, it is devised so that the positional deviation between the absorption grating 6 and the self-image of the phase grating 5 can be calculated. So, this point will be explained below.

Figure 10:
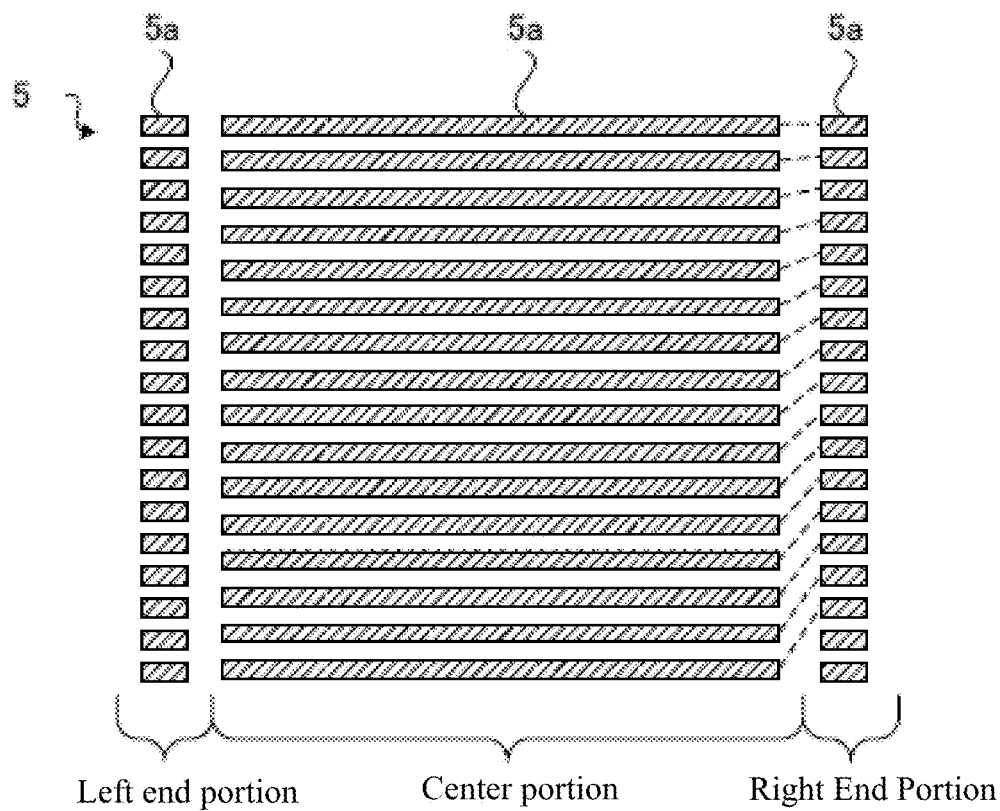
FIG. 10 is a schematic diagram explaining the configuration of the phase grating according to Example 1.

FIG. 10 explains the phase grating 5 described with reference to the left side of FIG. 2 in more detail. That is, assuming that the direction in which the absorption line 5a of the phase grating 5 extends is a lateral direction of the phase grating 5, the array pitch of the absorption line 5a at the left end and right end of the phase grating 5 is different from the array pitch of the absorption line 5a at the center part of the phase grating 5. As can be seen with reference to FIG. 10, the direction in which the absorption line 5a extends is a lateral direction in both end areas, and also is the same lateral direction in the central area. Also, the absorption line 5a at the left end portion of the phase grating 5 and the absorption line 5*a* at the central portion thereof are not continuous with each other. Between the array of the absorption lines 5*a* arranged in the vertical direction at the left end portion and the array of the absorption lines 5*a* arranged in the vertical direction at the central portion, a gap not having the absorption lines 5*a* is provided. In the same manner, the absorption line 5*a* at the right end portion of the phase grating 5 and the absorption line 5*a* at the central portion thereof are not continuous with each other. Between the array of the absorption lines 5*a* arranged in the vertical direction at the right end portion and the array of the absorption lines 5*a* arranged in the vertical direction at the central portion, a gap not having the absorption lines 5*a* is provided. The central portion corresponds to the subject area of the present invention, and both end portions each correspond to the reference area of the present invention.

The phase grating 5 according to the present invention is provided with a subject area which is an area provided with a predetermined repeating pattern for absorbing X-rays and through which an X-ray beam that passes through the subject passes and a reference area which is an area provided with a repeating pattern different from the subject area. The array pitch of the pattern repeated in the subject area is different from the array pitch of the pattern repeated in the reference area.

That is, the phase grating 5 according to Example 1 is provided with a center portion which is an area in which the absorption lines 5*a* each extending in one direction and absorbing X-rays are arranged in a direction orthogonal to the one direction and through which the X-ray beam that passes through the subject M passes and both end portions which is an area in which absorption lines 5*a* are arranged so that the pitch of the array is different from the center portion and through which the X-ray beam not passing through the subject M passes. In other words, the array pitch of the detection elements 4*p* in the vertical direction is not an integer multiple of the array pitch of the dark lines appearing at both end portions of the self-image of the phase grating 5.

Attention must be paid to the relationship between the array pitch of the detection elements 4*p* and the array pitch of the absorption lines 5*a* belonging to both the end portions of the phase grating 5. The self-image of the phase grating 5 is larger than the phase grating 5. Since X-rays spread radially from the X-ray source 3, the image of the phase grating 5 is enlarged and reflected on the detection surface 4*a*. The array pitch of the absorption line 5*a* of the phase grating 5 is set so as not to be the integer multiple of the array pitch of the dark lines of the self-image of the phase grating 5 appearing on the detection surface 4*a*, which does not mean that the array pitch of the detection elements 4*p* is not an integer multiple of the array pitch of the absorption lines 5*a*.

Figure 11:
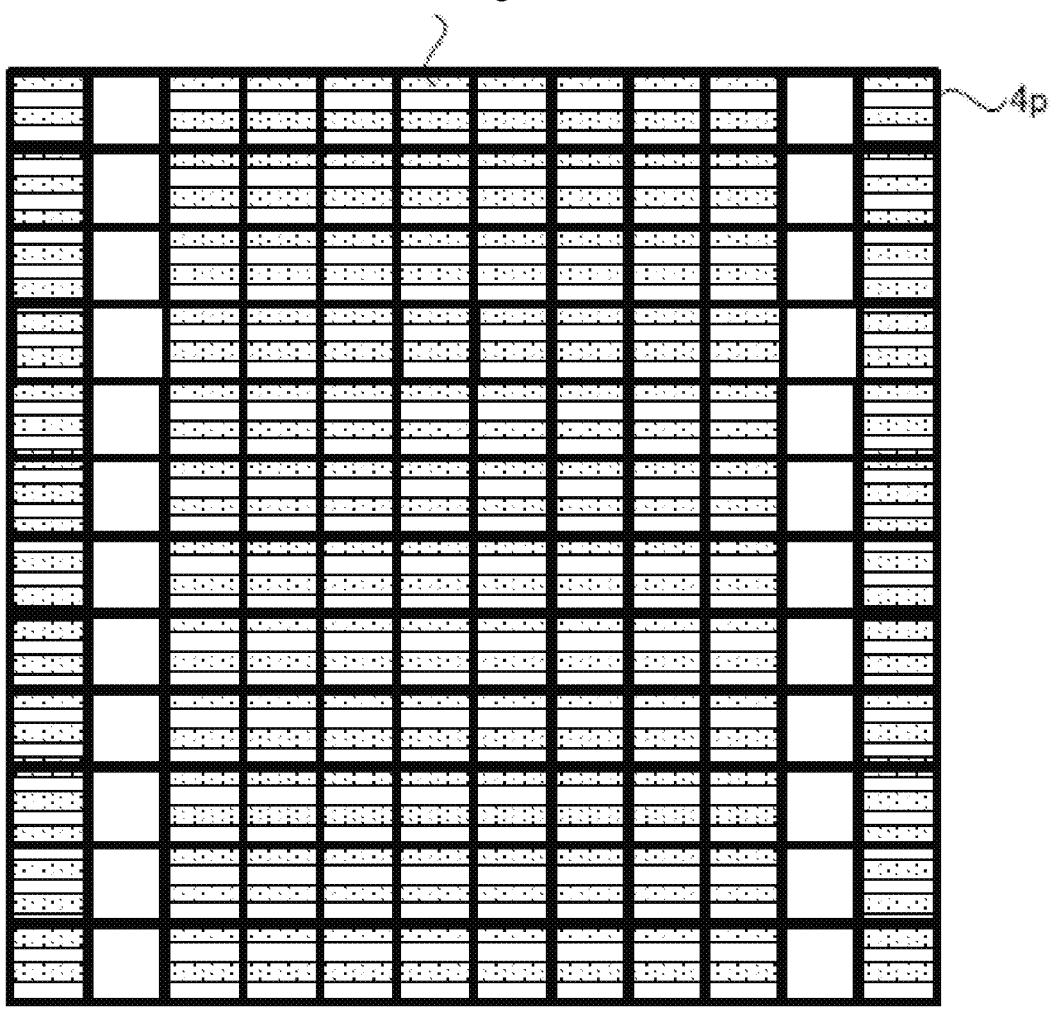
FIG. 11 is a plan view explaining how the self-image appears on the detection surface according to Example 1.

FIG. 11 is a diagram again showing how the self-image of the phase grating 5 appears on the detection surface 4*a*, and this time it also includes the end portions of the self-image of the phase grating 5. In FIG. 11, the detection element 4*p* on the detection surface 4*a* is highlighted with thick lines. As can be seen from this figure, in the detection surface 4*a*, assuming that the detection element 4*p* is divided into four rows for each of the detection elements 4*p* located at the portion where the central portion of the self-image is projected, one dark line appears at the first row, and one dark line appears at the third row. In the detection elements 4*p* located at the center, all of the self-image dark lines appear with this pattern. On the other hand, on the detection surface 4*a*, in each of the detection elements 4*p* located at the portions where both end portions of the self-image are projected, the dark line of the self-image does not appear as the same pattern. The position and number of appearance of the dark line of the self-image are different for each detection element 4*p*.

In both end portions of the self-image, the reason that the pattern of the dark line appearing on the detection element 4*p* is changed is that the array of absorption lines 5*a* arranged at both end portions of the self-image is devised. The array pitch of the dark lines constituting the self-image of the phase grating 5 on the detection surface 4*a* is different between the center portion of the self-image and both end portions. In the case of FIG. 11, the array pitch of the dark lines of the self-image at both end portions is shorter than the array pitch of the dark lines of the self-image at the center portion. Therefore, the position and number of dark lines appearing on the detection element 4*p* are not constant between detection elements 4*p*. It should be noted that the fact that the array pitch at both end portions is shorter than the array pitch at the center portion is merely an example of the embodiment. The array pitch at both end portions may be longer than the array pitch at the center portion. In other words, the array pitch of the dark lines of phase grating 5 at both end portions is not an integer multiple of the array pitch of the detection elements 4*p* and the absorption pitch of the absorption lines 6*a* of the absorption grating 6.

However, there is no doubt that the dark lines of the self-image and the detection elements 4*p* are arranged at a constant pitch, so the position and number of the dark lines appearing on the detection elements 4*p* do not differ at all detection elements 4*p*. Focusing on a certain detection element 4*p*, the appearance pattern of dark lines on the detection element 4*p* is taken as a reference pattern. Then, looking at each of the detection elements 4*p* of the detection element 4*p* arranged in the vertical direction, the appearance pattern of the dark line changes little by little from the reference pattern. After reaching a certain pattern, it approaches the reference pattern again and returns to the reference pattern. After that, this pattern change is repeated. Therefore, assuming that there is a certain detection element 4*p* located at the end portion of the self-image, detection elements 4*p* having the same position and number of dark lines appearing on the detection element 4*p* appear at equal intervals. For example, the detection elements 4*p* whose dark line appearance patterns are the same are located, for example, 20 positions apart in the vertical direction.

Note that the subject M in the X-ray phase contrast imaging apparatus of the present invention is configured to appear in the center portion of the self-image of the phase grating 5. Therefore, both end portions of the self-image of the phase grating 5 are the result of imaging of the X-rays not passing through subject M, and have no disturbance due to the influence of the subject M.

Figure 12:
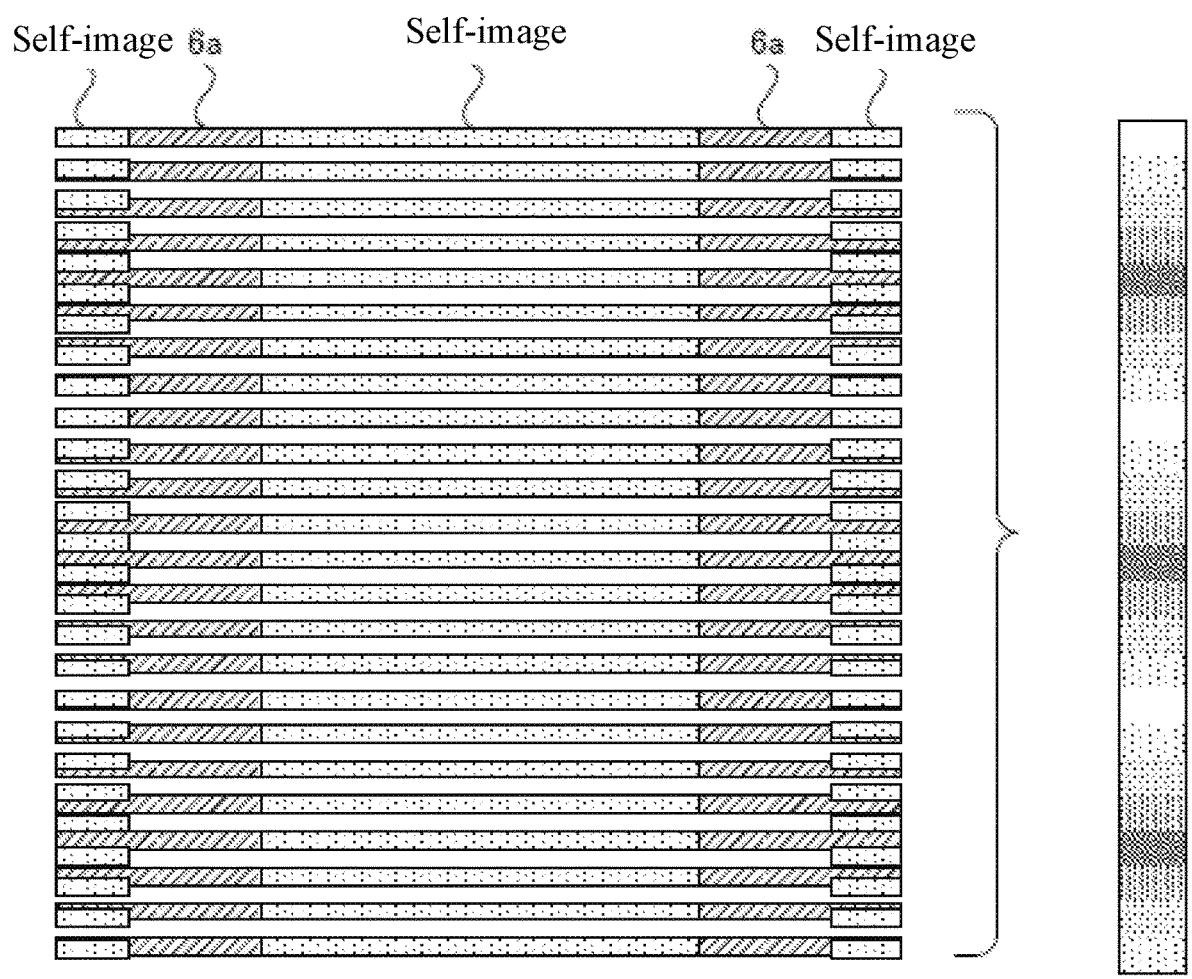
FIG. 12 is a plan view explaining how the interference fringe occurs between the self-image and the absorption grating according to Example 1.

FIG. 12 shows how the self-image of the phase grating 5 and the absorption grating 6 interfere at both end portions of the self-image. According to the explanation with reference to FIG. 6, the array pitch of the dark lines of the self-image of the phase grating 5 and the array pitch of the absorption lines 6*a* of the absorption grating 6 are identical on the detection surface 4*a* of the FPD 4, and therefore, the self-image of the phase grating 5 and the absorption grating 6 do not cause interference fringe with each other. This description is directed to the center portion of the self-image. Actually, at both end portions of the self-image, the absorption grating 6 and the self-image interfere with each other to cause an interference fringe as shown on the right side of FIG. 12. This is because at both end portions of the self-image, the array pitch of the self-image of the phase grating 5 is shorter than the array pitch of the absorption lines 6a of the absorption grating 6. In other words, this is because the array pitch of the dark lines of the phase grating 5 at both end portions is not an integer multiple of the array pitch of the absorption lines 6a of the absorption grating 6. Therefore, at both end portions of the self-image, the position of the dark line of the self-image appearing in the vicinity of each absorption line 6a is not constant between absorption lines 6a.

However, there is no doubt that the dark lines of the self-image and the absorption lines 6a are arranged at a constant pitch, so the position of the dark lines appearing in the vicinity of the absorption line 6a does not differ at all absorption lines 6a. For example, focusing on an absorption line 6a just overlapping the dark line of the self-image, when looking at each of the absorption lines 6a arranged in the vertical direction, the dark line gradually deviates from the absorption line 6a. Then, after the absorption line 6a and the dark line have reached a state in which they do not overlap, the absorption line 6a again overlaps the dark line, and the dark line just again overlaps the absorption line 6a. After that, this change is repeated. When the array pitch of the detection elements 4p is twice the array pitch of the absorption lines 6a, the dark line of the self-image just overlaps every 40 absorption lines 6a arrayed in the vertical direction.

FIG. 13 again shows the interference image obtained when imaging how the self-image of the phase grating 5 and the absorption grating 6 interfere while moving the absorption grating 6 in the array direction of the absorption lines 6a, and this time, it also includes the end portions of the self-image of the phase grating 5. In each interference image, an interference fringe appears at both end portions. At the center portion of the interference image, the center portion of the self-image of the phase grating 5 appears. The fact that no interference fringe appears in this portion has already been explained with reference to FIG. 6. At both end portions of the self-image of the phase grating 5, both end portions of the interference image appear. The fact that an interference fringe appears in this portion has already been explained with reference to FIG. 12.

Figure 13:
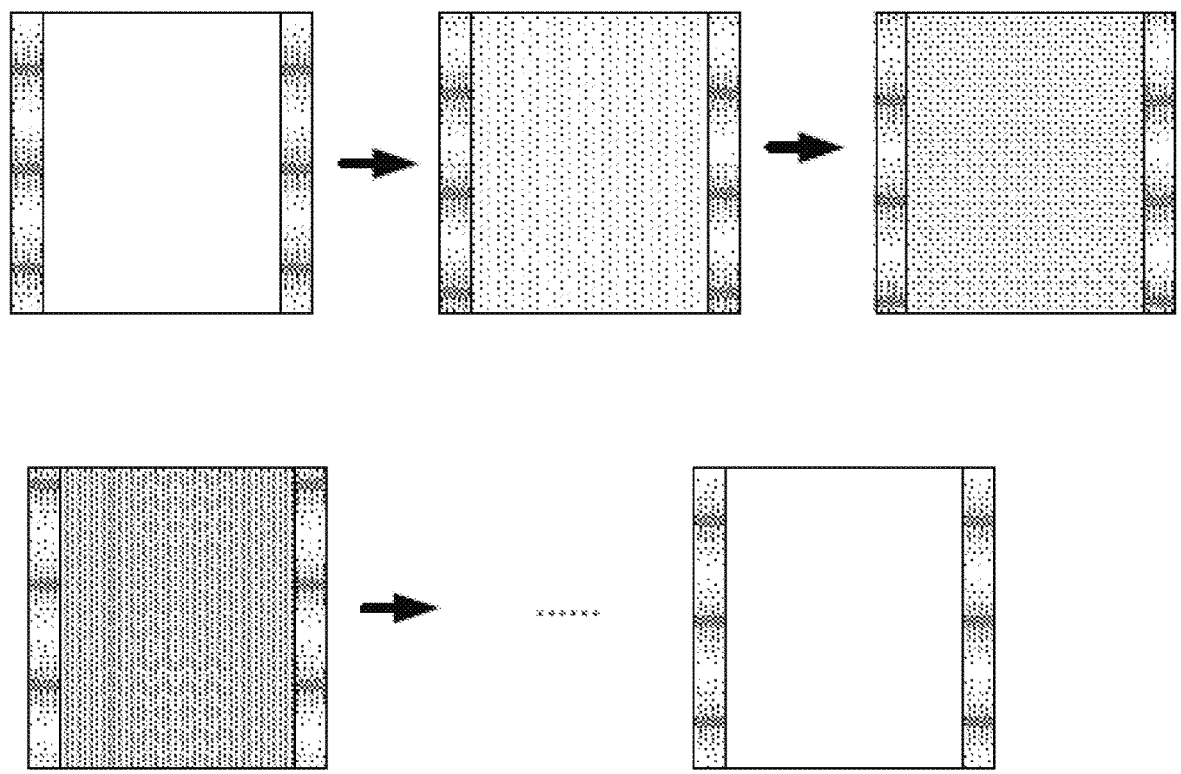
FIG. 13 is a plan view explaining how the interference fringe moves in accordance with the relative movement of the absorption grating and the self-image according to Example 1.

Let's focus on the center portion of each interference image. As the interference image is continuously captured while moving the absorption grating 6, an interference image bright at the center portion is acquired at the beginning of the continuous imaging as shown in FIG. 13. Eventually, the center portion of the obtained interference image gets darker gradually. After it gets the darkest, it gradually gets brighter and returns to its original brightness. Such a change in the brightness of the interference image at the center position is caused by the relative movement between the absorption grating 6 and the self-image of the phase grating 5 described with reference to FIG. 5.

Next, let's focus on both end portions of each interference image. At both end portions of each interference image, the interference fringe caused by the interference of the self-image of the phase grating 5 and the absorption grating 6 is reflected as shown in FIG. 13. This interference fringe is configured by alternatingly arranging bright and dark areas. At the beginning of continuous imaging, the bright portion of the interference fringe is located at the upper end of the interference image. As the continuous imaging is performed, the light portion gradually moves toward the lower side of the interference image. As the continuous imaging is further performed, the upper end of the interference image returns to the bright portion again. Such a movement of the interference fringe is caused by the relative movement of the absorption grating 6 and the self-image of the phase grating 5 described with reference to FIG. 12. In the bright portion appearing in the interference fringe, the absorption line 6a of the absorption grating 6 and the dark line of the self-image just overlap each other. When the absorption grating 6 is moved relative to the self-image, the place where the absorption line 6a and the dark line of the self-image just overlap moves toward the lower side of the self-image. As a result, the bright portion in the interference fringe on the interference image also moves downward following this.

Figure 14:
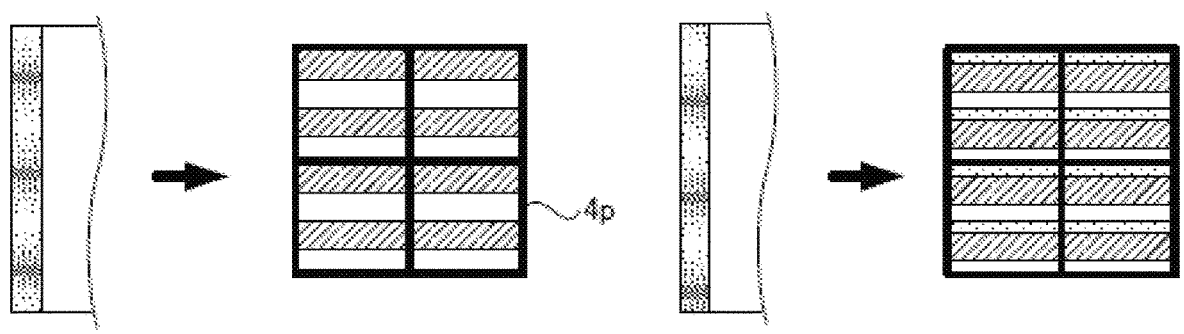
FIG. 14 is a schematic diagram explaining the relationship between the positional relationship between the absorption grating and the self-image and the appearance position of the interference fringe according to Example 1.

By examining the appearance position of the interference fringe on the interference image, it becomes possible to know the positional relationship between the absorption grating 6 and the self-image of the phase grating 5 when this interference image is captured, so this point will be explained. The left side of FIG. 14 shows the state in which the bright portion of the interference fringe appears at the upper end of the interference image at both ends of the interference image. At this time, in the center portion of the self-image of the phase grating 5, as illustrated, the absorption line 6a of the absorption grating 6 and the dark line of the phase grating 5 are just overlapped. On the other hand, the right side of FIG. 14 shows the state in which the bright portion of the interference fringe appears at a position shifted slightly downward from the upper end of the interference image at both ends of the interference image. At this time, in the center portion of the self-image of the phase grating 5, as illustrated, the absorption line 6a of the absorption grating 6 and the dark line of the phase grating 5 are slightly shifted from the overlapped state.

Figure 15:
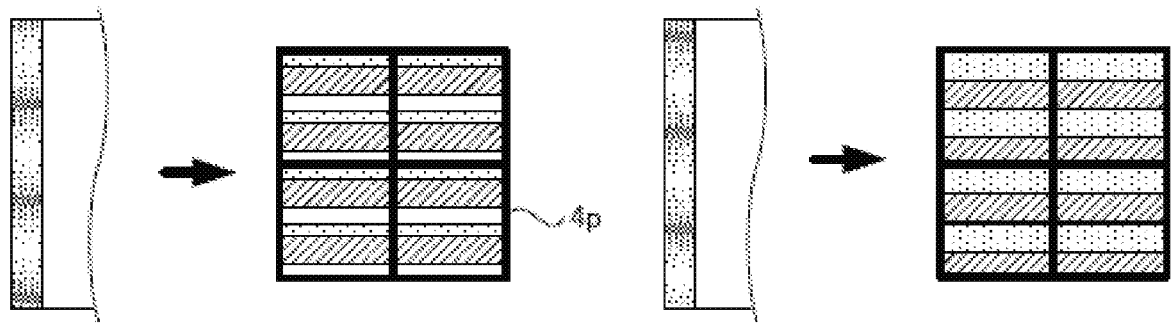
FIG. 15 is a schematic diagram explaining the relationship between the absorption grating and the self-image and the appearance position of the interference fringe according to Example 1.

The left side of FIG. 15 shows the state in which the bright portion of the interference fringe is further shifted downward from the state shown in the right side of FIG. 14 at both ends of the interference image. At this time, in the center portion of the self-image of the phase grating 5, as illustrated, the absorption line 6a of the absorption grating 6 and the dark line of the phase grating 5 are further shifted. On the other hand, the right side of FIG. 15 shows the state in which the bright portion of the interference fringe appears at a position further shifted toward the lower side of the interference image at both ends of the interference image. At this time, in the center portion of the self-image of the phase grating 5, as illustrated, the absorption line 6a of the absorption grating 6 and the dark line of the phase grating 5 are not overlapped.

The position calculation unit 11 in FIG. 1 detects the relative position of the self-image of the phase grating 5 with respect to the absorption grating 6 based on the above-described principle. At both ends of the consecutively captured interference image, the interference fringe inherent in the interference image is reflected.

Therefore, the position calculation unit 11 can detect the relative position of the self-image of the phase grating 5 with respect to the absorption grating 6 for each of the interference images. The position calculation unit 11 calculates the relative position of the phase grating 5 and the absorption grating 6 on the basis of the difference in the detected amount of X-rays that differs between detection elements 4p located in the area where both end portions of the phase grating 5 on the detection surface 4a appear. The position calculation unit 11 detects the moire (interference fringe) occurring between the image of the pattern of the reference area appeared on the detection surface and the pattern on the absorption grating and calculate the relative position between the phase grating 5 and the absorption grating 6. Further, at this time, the position calculation unit 11 also calculates the position of the X-ray source 3 with respect to the phase grating 5 and the absorption grating 6. This is because the way of appearing the interference fringe changes depends on the relative position of the three members, i.e., the X-ray source 3, the phase grating 5, and the absorption grating 6.

The detection result on the relative position of the self-image of the phase grating 5 with respect to the absorption grating 6 detected by the position calculation unit 11 is sent to the self-image generation unit 12 together with the interference image. Based on the detection result of the relative position corresponding to the interference image, the self-image generation unit 12 corrects the calculation related to the self-image generation, generates a self-image of the phase grating 5, and generates a self-image in which the self-image is reflected. The self-image generation unit 12 is configured to generate an image of the phase grating 5 based on an image in which the images of the phase grating 5 obtained by continuous image capturing while changing the positional relationship between the image of the phase grating 5 and the absorption grating 6 are overlapped. The self-image generation unit 12 according to the present invention is characterized in that a correction is performed by referring to the calculated relative position particularly when generating an image of the phase grating 5 based on the output of the FPD 4.

The generated self-image image is sent to the fluoroscopic image generation unit 13. The fluoroscopic image generation unit 13 generates a fluoroscopic image in which the distribution of the phase contrast inside the subject M is imaged based on the self-image. Based on this operation, the operation of the X-ray phase contrast imaging apparatus of the present invention is completed.

<Reason for Reflecting Interference Fringe at Both Ends of Interference Image>

Figure 16:
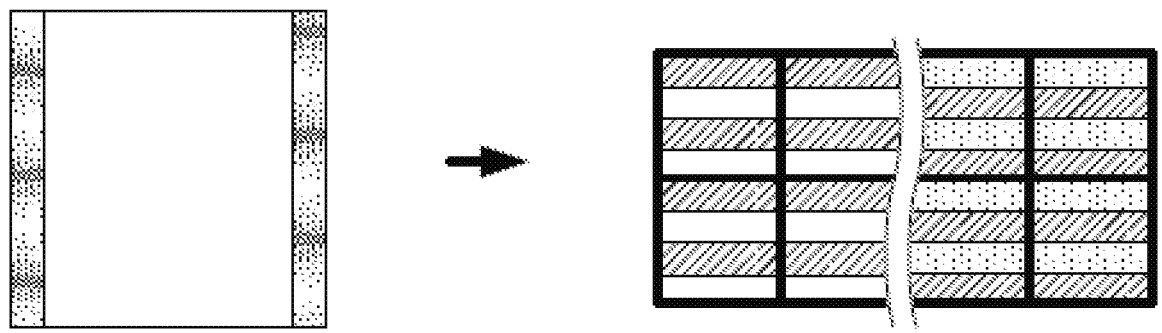
FIG. 16 is a schematic diagram explaining the advantage of generating the interference fringe at both ends of the image according to Example 1.

Next, the necessity of reflecting the interference fringe at both ends of the interference image will be explained. By reflecting the interference fringe at both ends of the interference image, it is possible to grasp how much the self-image of the phase grating 5 is inclined with respect to the absorption grating 6. For example, as described in FIG. 16, it is assumed that the interference fringe appeared on the left side of the interference image and the interference fringe appeared on the right side of the interference image are deviated from each other in the vertical direction of the interference image. The interference fringe appeared on the left side of the interference image in FIG. 16 is actually the same as the interference fringe described with reference to the left side of FIG. 14. Therefore, the left end of the center portion of the self-image of the phase grating 5 is in a state in which the absorption line 6a just overlaps the self-image as shown in FIG. 16. Further, the interference fringe appeared on the right side of the interference image in FIG. 16 is actually the same as the interference fringe described with reference to the right side of FIG. 15. Therefore, the right end of the center portion of the self-image of the phase grating 5 is in a state in which the absorption line 6a does not overlap the self-image as shown in FIG. 16.

In this way, by generating the interference fringe at both ends of the self-image of the phase grating 5, it is possible to individually determine the positional relationship between the absorption grating 6 and the self-image of the phase grating 5 at the right end of the center portion of the phase grating 5 and the positional relationship between the absorption grating 6 and the self-image of the phase grating 5 at the left end of the center portion of the phase grating 5. By measuring these two positional relationships, it is possible to grasp how much the self-image of the phase grating 5 is inclined with respect to the absorption grating 6. The inclination situation of the self-image is calculated by the position calculation unit 11. In cases where it turns out that the self-image is excessively inclined, for example, the phase grating 5 is rotated to correct the inclination of the self-image of the phase grating 5, so that the continuous image capturing of the interference image can be continuously performed.

<Subject Rotation Mechanism>

The subject rotation mechanism 17 is provided for the purpose of rotating the subject M with respect to each of the parts 3, 4, 5, and 6. The subject rotation control unit 18 is provided for the purpose of controlling the subject rotation mechanism 17.

<Tomographic Image Generation Unit>

A plurality of fluoroscopic images generated while rotating the subject M is sent to the tomographic image generation unit 14. The tomographic image generation unit 14 reconstructs a plurality of fluoroscopic images to generate a tomographic image of the subject M in which the phase contrast distribution of the subject M is mapped. In order to generate one fluoroscopic image, it is necessary to perform image capturing of the self-image a plurality of times. Therefore, in order to acquire the tomographic image, a considerable number of self-images have to be captured. In the course of repeatedly performing the image capturing of the self-image in this way, the part for fixing the phase grating 5 thermally expands, which moves the self-image of the phase grating 5 little by little on the detection surface 4a. According to the present invention, even if such a situation occurs, since the positional relationship between the self-image and the absorption grating 6 can be actually measured for each self-image capturing, it is possible to generate a tomographic image without being affected by the movement of the self-image. As described above, in the present invention, CT imaging of the subject M can also be performed.

Each of the parts 11, 12, 13, 14, 16, and 18 according to the present invention is realized by executing various programs by the CPU provided in the apparatus. Instead of the CPU, each part may be realized by an individual microcomputer.

As described above, according to the present invention, it is possible to provide an X-ray imaging apparatus capable of performing precise imaging without performing pre-imaging in the absence of the subject M. That is, the apparatus of the present invention is provided with the phase grating 5 in which a center portion and both end portions are provided. Although grating absorbers are arrayed in each area, their array pitches are different. The image (grating image) of the phase grating 5 focused on the detection surface interferes with the absorption grating 6 provided so as to cover the detection surface. In image capturing with a fringe scanning method or an edge illumination method, since no interference fringe occurs in the portion where the center portion of the detection surface appears. Therefore, in cases where no subject M is arranged, there is no difference in the detection amount of X-rays between detection elements 4p.

However, in the portions where both end portions of the phase grating 5 on the detection surface 4a appear, the self-image of the phase grating 5 and the absorption grating 6 interfere and an interference fringe occurs. The appearance position of this interference fringe represents the relative position between the self-image and the absorption grating 6 on the detection surface. Both end portions of the phase grating 5 are reflected in the captured interference image, and in the interference image, the center portion of the phase grating 5 is located in a different part. For this reason, according to the present invention, there is no need to separately perform image capturing in the absence of the subject M to grasp the relative position between the phase grating 5 and the absorption grating 6. This is because in the interference image, an interference fringe representing the relative position between the self-image and the absorption grating 6 appears apart from the area in which the subject M appears.

Further, when the reference area is provided at both ends of the phase grating 5, not only the positional displacement between the phase grating 5 and the absorption grating 6 but also the rotation angle of the absorption grating 6 with respect to the phase grating 5 can be calculated. Further, in the same manner, it becomes possible to calculate not only the positional displacement between the phase grating 5 and the FPD 4 but also the rotation angle between the phase grating 5 and the FPD 4.

The present invention is not limited to the above-described configuration and may be modified as follows.

Figure 17:
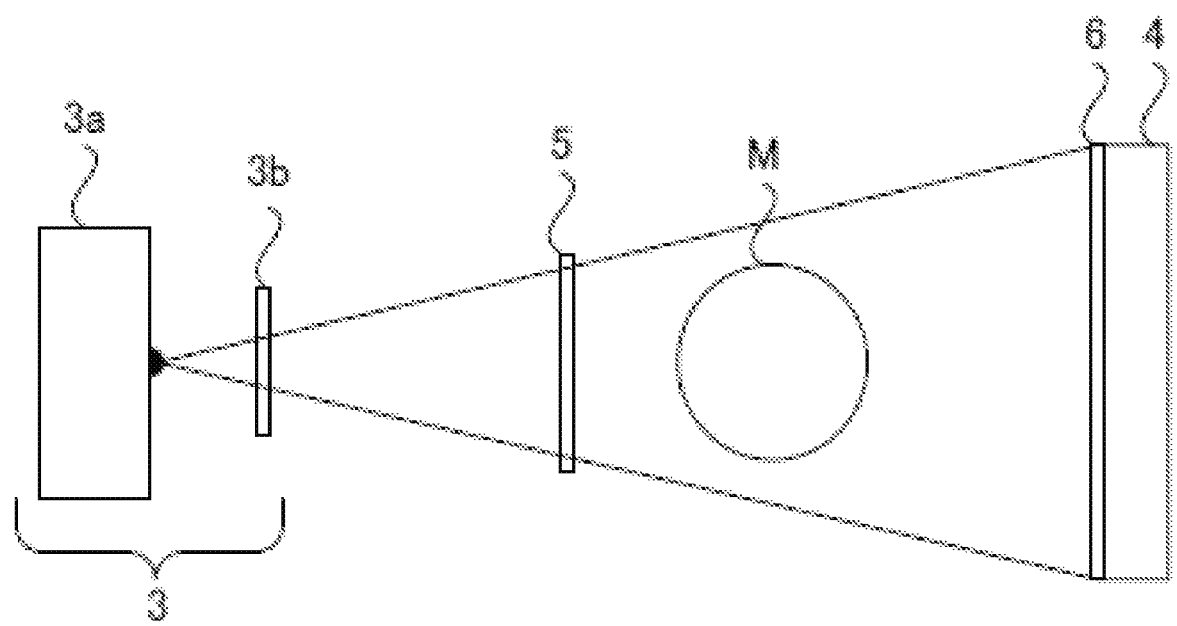
FIG. 17 is a schematic diagram explaining one modified Example according to the present invention.

(1) According to the configuration of Example 1, it is configured such that the absorption grating 6 moves with respect to the FPD 4, but the present invention is not limited to this configuration. As shown in FIG. 17, the present invention may be applied to an X-ray phase contrast imaging apparatus in which the absorption grating 6 is fixed to the FPD 4. In FIG. 17, an X-ray phase contrast is imaged by a method called a moire single imaging method.

Figure 18:
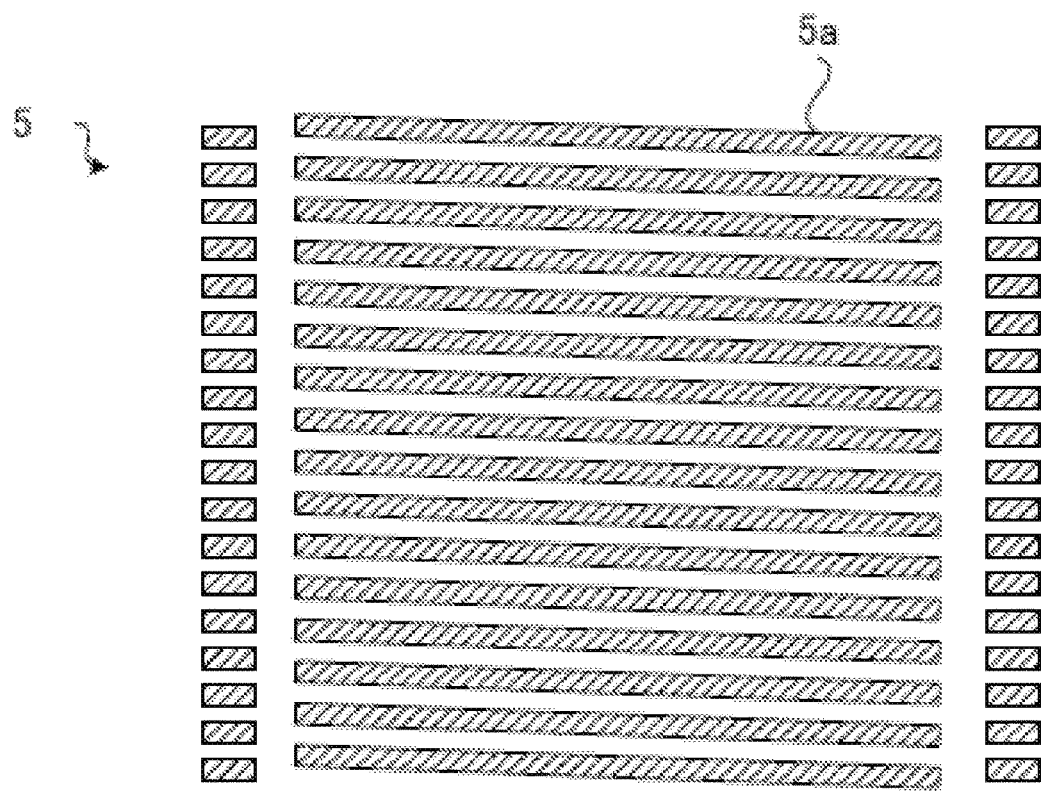
FIG. 18 is a schematic diagram explaining one modified Example according to the present invention.

FIG. 18 shows a phase grating 5 according to this modified example. In the same manner as in Example 1, the phase grating 5 according to this modified example is also provided with a center portion that passes an X-ray beam which passes through the subject M and both end portions that pass an X-ray beam which does not pass through the subject M. Among them, the configuration of both end portions is the same as that of the phase grating 5 of Example 1. On the other hand, in the center portion of the phase grating 5 according to this modified example, the absorption line 5a of the phase grating 5 is inclined with respect to the direction that the absorption line 6a of the absorption grating 6 extends. The array pitch of the absorption lines 5a of the phase grating 5 is the same as the array pitch of the absorption lines 6a. However, in this modified example, the direction of the array differs between the absorption line 6a and the absorption line 5a in the center portion of the phase grating 5. In this modified example, the direction that the grating absorber extends in the center portion of the phase grating 5 is inclined from the direction that the grating absorber extends at both end portions of the phase grating 5, and the direction that the absorption line 6a in the absorption grating 6 extends coincides with the direction that the grating absorber at both end portions of phase grating 5 extends.

According to this modified example, it is possible to perform imaging of the self-image of the phase grating 5 without moving the absorption grating 6 with respect to the FPD 4. According to this modified example, since the phase grating 5 is inclined with respect to the absorption grating 6, an interference fringe occurs between the absorption grating 6 and the phase grating 5. It should be careful that this interference fringe is about the self-image related to the center portion of the phase grating 5 and is different from the interference fringe about the self-image at the end portion of the phase grating 5 described with reference to FIG. 12.

Figure 19:
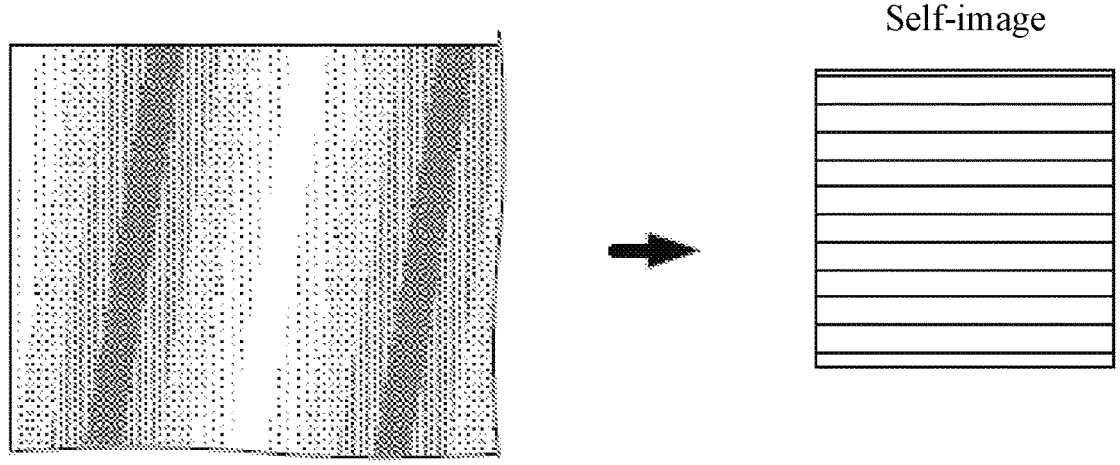
FIG. 19 is a schematic diagram for explaining one modified example according to the present invention.

Therefore, when a self-image is captured, as shown in FIG. 19, an interference image in which an interference fringe spreads all over is acquired. Note that in FIG. 19, the interference fringe described with reference to FIG. 12 that should appear at both ends of the interference image is not illustrated. In fact, the interference image obtained in FIG. 19 can be regarded as a single interference image obtained by combining a plurality of interference images different in the relative position between the self-image of the phase grating 5 and the absorption grating 6 described with reference to FIG. 7 in a stripe form. Therefore, the self-image generation unit 12 can generate a self-image based on the interference image of the interference fringe obtained in FIG. 19. Even in this modified example, unless the relative position between the self-image of the phase grating 5 and the absorption grating 6 is precisely known, a self-image cannot be generated correctly. However, according to the present invention, since it is devised so that an interference fringe occurs at both end portions of the self-image of the phase grating 5, based on the appearance position of this interference fringe, it is possible to exactly know the relative position between the self-image of the phase grating 5 and the absorption grating 6.

As described above, the present invention can be applied to an apparatus related to a moire single imaging method as described above. In the moire single imaging method, an interference fringe also occurs at the center portion, so it is not impossible in principle to know the relative position between the absorption grating 6 and the grating image using the method. However, the interference fringe appearing in the center portion of the self-image of the phase grating by the moire single imaging method is not suitable for finding the relative position between the absorption grating 6 and the grating image because the pitch is too fine. According to the present invention, it is configured such that both end portions in which the pitch of the grating absorber is adjusted so that a pattern of the interference fringe suitable for knowing the relative position is generated are provided separately from the center portion. So, it is possible to accurately know the positional relationship between the grating image and the absorption grating 6.

Figure 20:
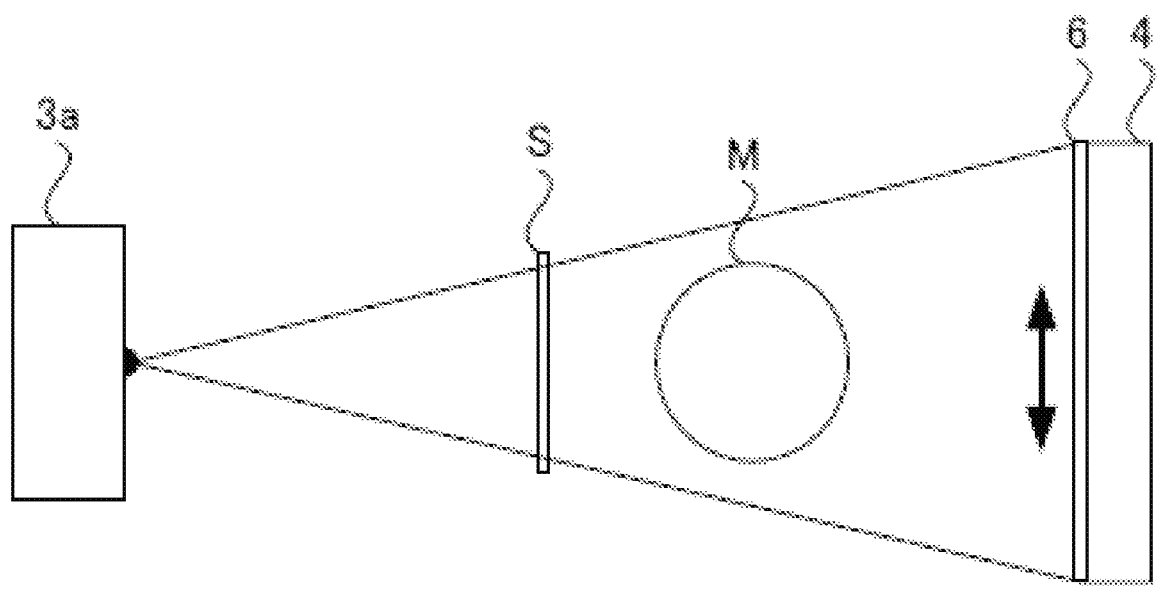
FIG. 20 is a schematic diagram for explaining one modified example according to the present invention.

(2) The principle of the present invention can also be applied to a device other than a device utilizing Talbot interference. Hereinafter, a modified example in which the present invention is applied to an edge illumination imaging apparatus will be described. FIG. 20 shows an apparatus configuration related to an edge illumination imaging apparatus. In this configuration, the multi-slit 3b is not provided, and the shadow of the grating S is reflected on the FPD 4. This grating S is provided in place of the phase grating 5 in Example 1, and has the same shape as that of the phase grating 5 described in FIG. 10. Note that the phase grating in Example 1 is a term used when describing Talbot interference. In this modified example, it is merely called a grating S since no Talbot interference is utilized. However, the array pitch of the absorption lines in the grating S is wider than the array pitch of the absorption lines 5a in the phase grating 5.

Figure 21:
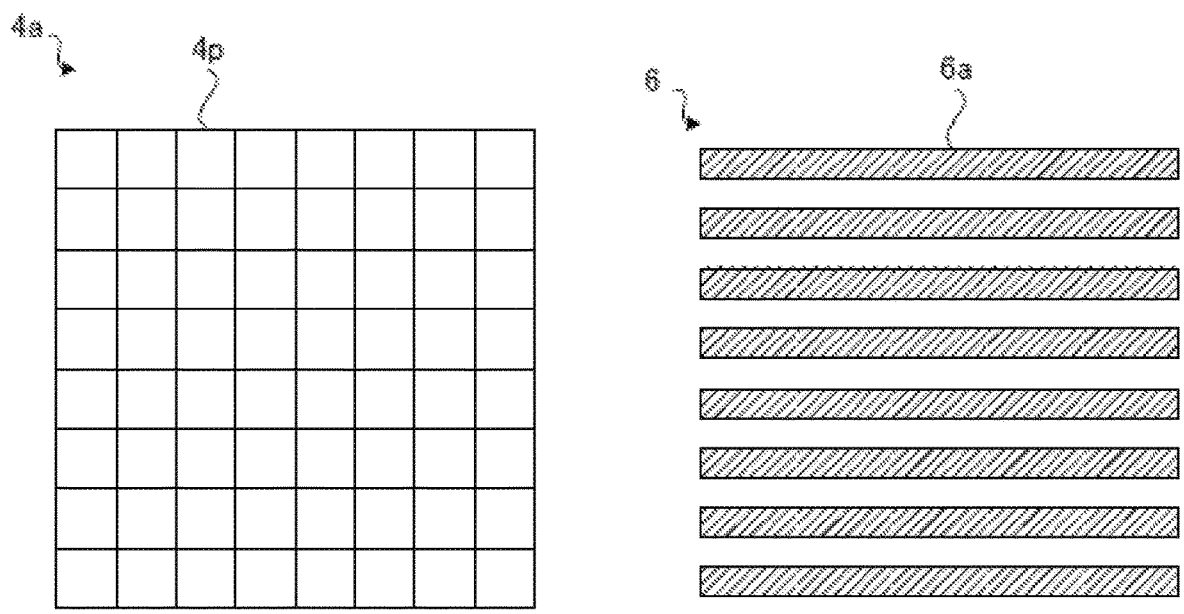
FIG. 21 is a schematic diagram for explaining one modified example according to the present invention.

FIG. 21 shows the configuration of the detection surface and the absorption grating 6 of the FPD 4 in this modified example. In the same manner as in the configuration of Example 1, the detection surface 4a of the FPD 4 is configured by arranging detection elements 4p in matrix. On the other hand, the absorption line 6a of the absorption grating 6 extends in the lateral direction of the detection surface 4a in the same manner as in Example 1, and is arrayed in the vertical direction of the detection surface 4a. However, the gap of the adjacent absorption lines 6a in the vertical direction is half the width of the detection element 4p, and the width of the absorption line 6a in the array direction is half the width of the detection element 4p.

Therefore, the absorption lines 6a are arrayed in the vertical direction at an array pitch corresponding to one detection element 4p. The absorption grating 6 is aligned with the FPD 4 so that the absorption line 6a is positioned so as to straddle the adjacent detection elements 4p.

The edge illumination imaging device is configured to generate an interference image related to the internal structure of the subject M by repeating the image capturing twice. This point will be briefly described.

Figure 22:
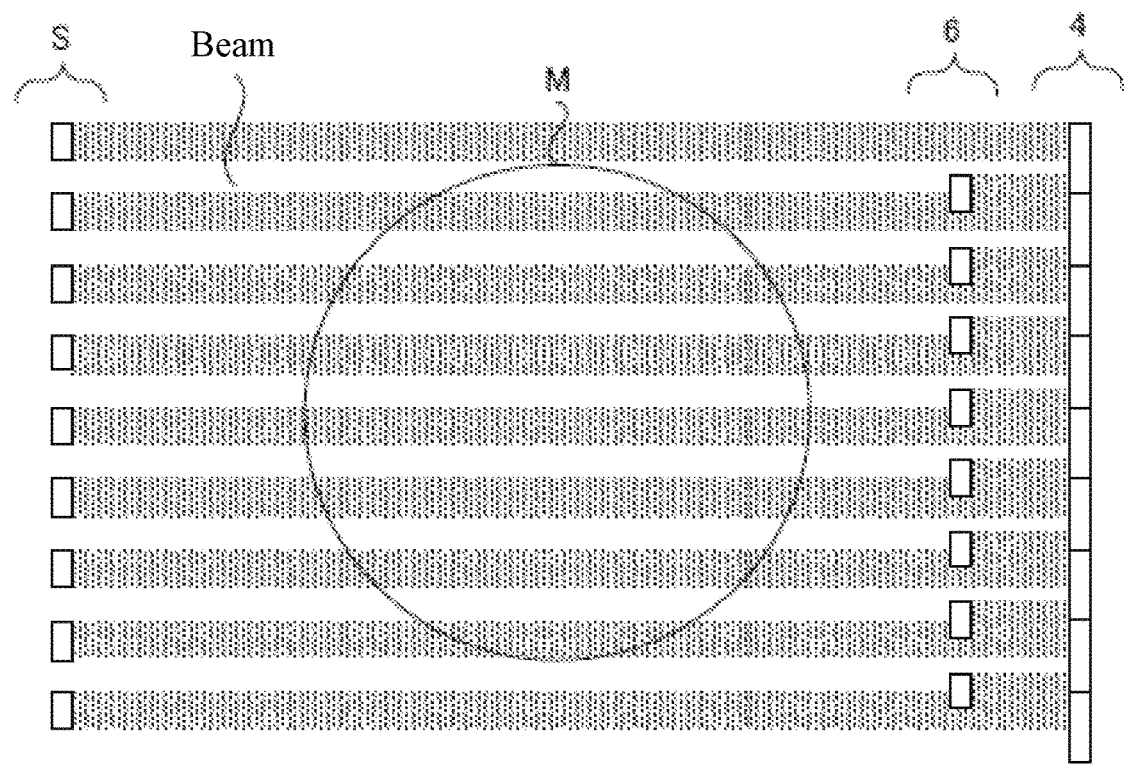
FIG. 22 is a schematic diagram for explaining one modified example according to the present invention.

FIG. 22 shows a first image capturing of two image capturing. The X-rays that have passed through the grating S becomes a striped beam, passes through the subject M, and is incident on the absorption grating 6. The striped beam is configured by an array of an X-ray beam that has passed through the slit and is elongated in shape and has a width half the width of the detection element 4p of the FPD 4. Since the absorption grating 6 is located at the position where the lower half of each of the elongated X-ray beams is incident on the absorption line 6a, each of the elongated X-ray beams is absorbed in the lower half, narrowed further and enters the FPD 4. This X-ray beam further narrowed in width is incident on a certain detection element 4p. At this time, the X-ray beam is configured to be incident on the center portion of the detection element 4p. The detection element 4p on which this X-ray beam is incident will be referred to as a detection element 4p of an incident target.

Figure 23:
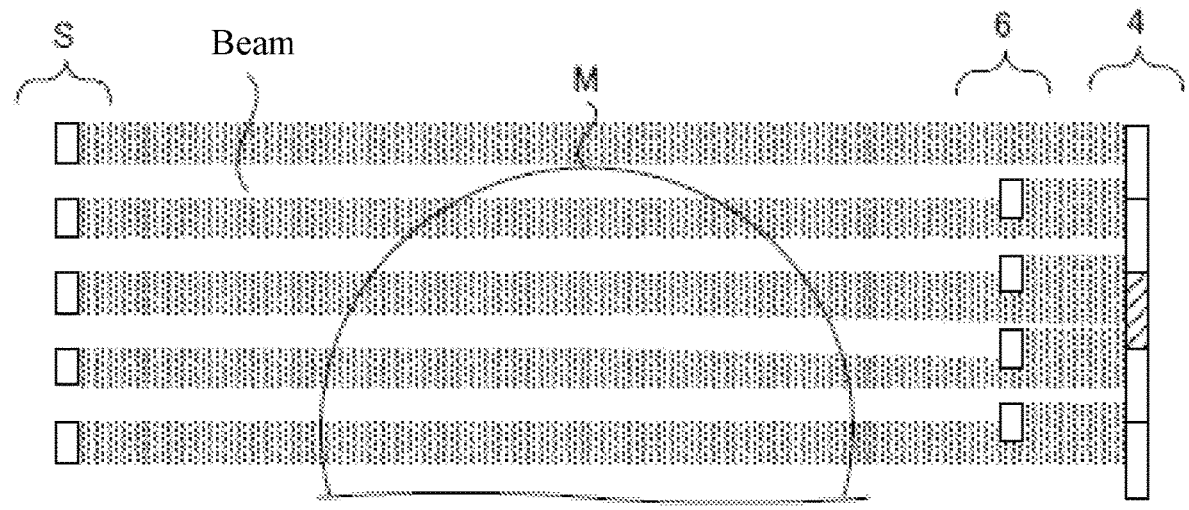
FIG. 23 is a schematic diagram for explaining one modified example according to the present invention.

In cases where the subject M is not placed between the grating S and the absorption grating 6, the X-ray beam is merely incident on the center portion of the detection element 4p. However, when a subject M is placed between the grating S and the absorption grating 6, the traveling direction changes while the X-ray beam passes through the subject M. As shown in FIG. 23, when the elongated X-ray beam is bent downward, the X-ray beam is incident in a manner shifted in the downward direction of the detection element 4p of the incident target. However, the X-ray beam is prevented by the absorption line 6a of the absorption grating 6 from reaching the detection element 4p of the incident target indicated by hatching. From the output of the detection element 4p of the incident target, it is possible to know how much the X-ray beam is bent downward. Based on this principle, the edge illumination imaging device captures the interference image showing the degree to which the X-ray is bent in a downward direction.

Before subsequently performing the next second image capturing, the FPD 4 and the absorption grating 6 are moved upward by half of the detection element 4p with respect to the stripe-shaped X-ray beam. By this operation, the positional relationship between the striped beam and the absorption grating 6 changes.

Figure 24:
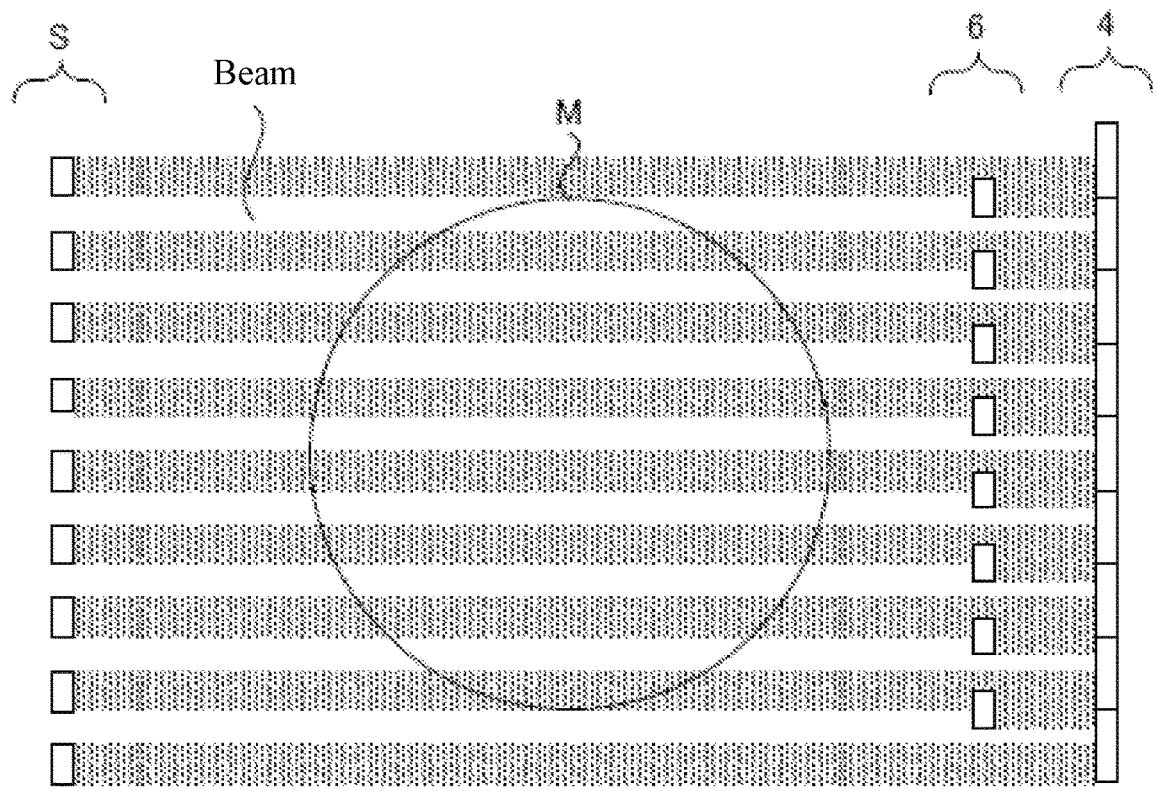
FIG. 24 is a schematic diagram explaining one modified Example according to the present invention.

FIG. 24 shows a second image capturing of two image capturing. The X-rays which has passed through the grating S becomes a striped beam, passes through the subject M, and is incident on the absorption grating 6. The striped beam is configured by an array of X-ray beams that have passed through the slit and are formed in an elongated shape. Since the absorption grating 6 is located at the position where the upper half of each of the elongated X-ray beams is incident on the absorption line 6a, each of the elongated X-ray beams is absorbed by the lower half, narrowed further and enters the FPD 4. This X-ray beam further narrowed in width is incident on a certain detection element 4p. At this time, the X-ray beam is configured to be incident on the center portion of the detection element 4p. The detection element 4p on which this X-ray beam is incident will be referred to as a detection element 4p of an incident target.

Figure 25:
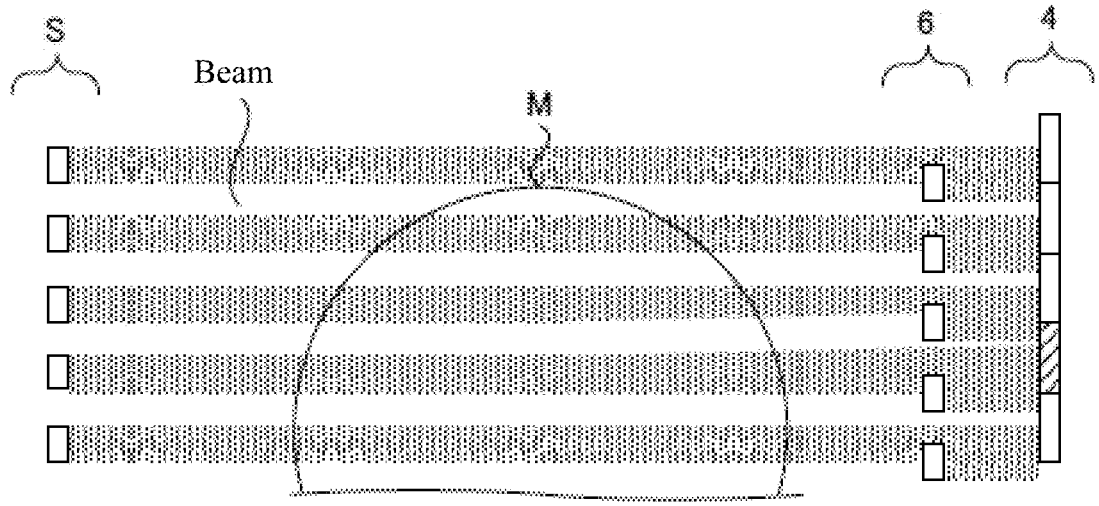
FIG. 25 is a schematic diagram explaining one modified Example according to the present invention.

In cases where the subject M is not placed between the grating S and the absorption grating 6, the X-ray beam is merely incident on the lower half of the detection element 4p. However, when a subject M is placed between the grating S and the absorption grating 6, the traveling direction changes while the X-ray beam passes through the subject M. As shown in FIG. 25, when the elongated X-ray beam is bent downward as shown in the arrow, the X-ray beam is incident in a manner shifted in the upward direction of the detection element 4p of the incident target. However, the X-ray beam is prevented by the absorption line 6a of the absorption grating 6 from reaching the detection element 4p of the incident target indicated by hatching. From the output of the detection element 4p of the incident target, it is possible to know how much the X-ray beam is bent in the upward direction. Based on this principle, the edge illumination imaging device captures the interference image showing the degree to which the X-ray is bent in an upward direction.

The edge illumination imaging device generates an interference image in which the changes in the travelling direction of the X-ray by the subject M are imaged based on two captured interference images.

Also in this modified example, the interference fringe indicating the relative position between the shadow of the grating S and the absorption grating 6 appears at both ends of the interference image (see FIG. 12). According to the apparatus of the present invention, even if the relative position between the shadow of the grating S and the absorption grating 6 is not ideal, without being affected by that, it is possible to perform accurate imaging of the inside of the subject M.

(3) The principle of the present invention can also be applied to an edge illumination imaging device having no absorption grating 6. The device according to this modified example is equipped with an X-ray detector having a scintillator which causes fluorescence when X-rays are incident. In such an X-ray detector, detection elements are arranged in a two-dimensional matrix. This detection element is configured to detect fluorescence caused by a scintillator. An X-ray detector of this type is called an indirect type detector. A layer in which the detection elements are arranged will be called a two-dimensional matrix layer.

Figure 26:
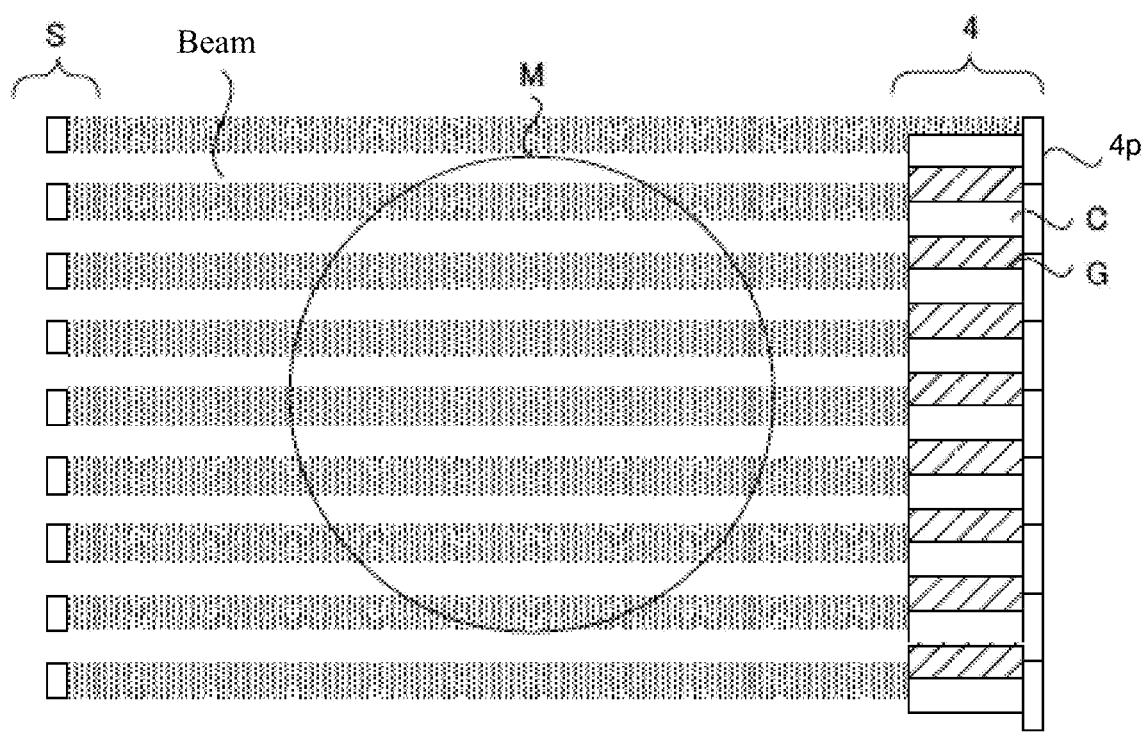
FIG. 26 is a schematic diagram explaining one modified Example according to the present invention.

FIG. 26 shows how the edge illumination imaging is performed using the X-ray detector of this modified example. The FPD 4 in this modified example has alternative layers formed by alternately arranging a scintillator element C having a width half of the detection element 4p and a glass element G having a width half of the detection element 4p. The scintillator element is made of a material that emits fluorescence when X-rays are incident, and the glass element G is made of glass that does not emit fluorescence even when X-rays are incident. The alternative layers are aligned with the two-dimensional matrix layer so that the scintillator elements straddle the adjacent detection elements 4p.

With the configuration of FIG. 26, it is possible to perform the same imaging as in the above-described FIG. 22. That is, in the detection element 4p of FIG. 22, the portion where the absorption line 6a of the absorption grating 6 is provided corresponds to the portion where the glass element G of the alternative layer is provided in the detection element 4p of FIG. 26. In addition, in the detection element 4p of FIG. 22, the portion exposed from the absorption line 6a corresponds to the portion where the scintillator element C of the alternative layer is provided in the detection element 4p of FIG. 26. Therefore, by using the configuration of FIG. 26, it is possible to capture an interference image showing the degree to which the X-rays bend downward.

The configuration of this modified example is also configured to perform the image capturing of the interference image twice. After the image capturing according to FIG. 26 is completed, before the subsequent second image capturing is performed, the FPD 4 is moved upward by half of the detection element 4p with respect to the stripe-shaped X-ray beam. By this operation, the positional relationship between the striped beam and the FPD 4 changes as shown in FIG. 27.

Figure 28:
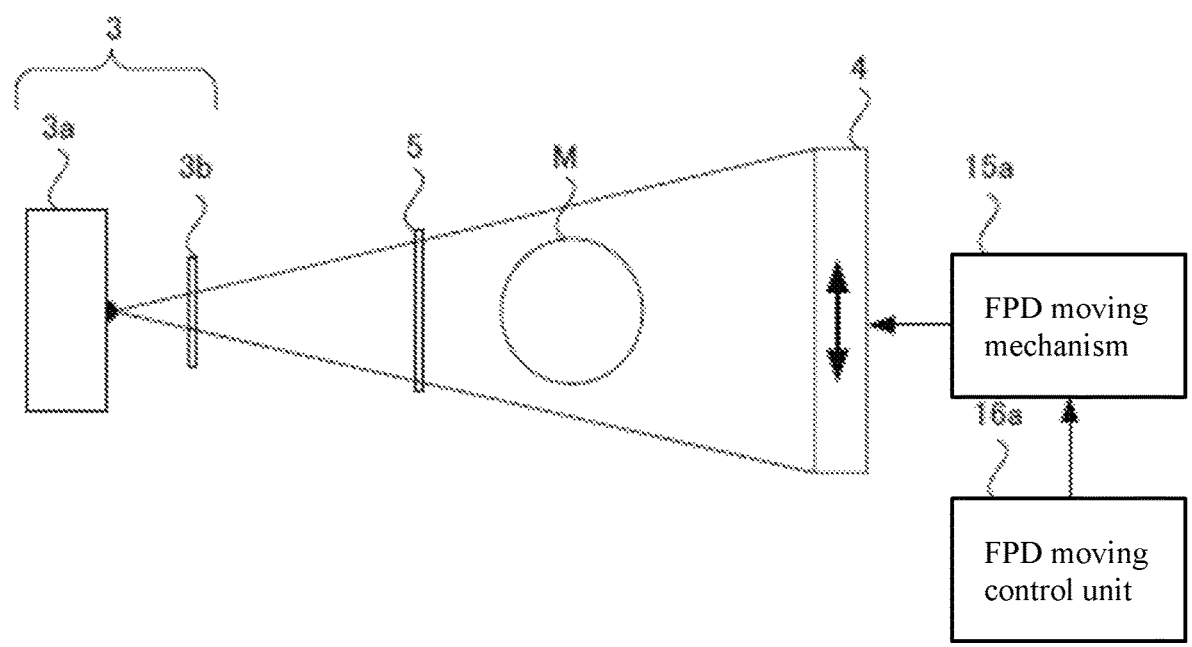
FIG. 28 is a schematic diagram explaining one modified Example according to the present invention.

FIG. 28 illustrates the configuration for moving the FPD 4. The FPD moving mechanism 15a is configured to move the FPD 4, and the FPD movement control unit 16a is configured to control the FPD moving mechanism 15a. The FPD moving mechanism 15a is provided for the purpose of changing the relative position between the self-image of the phase grating 5 and the FPD 4. The change of this relative position is the same as in Example 1 in that it can be realized by moving the X-ray source 3, the multi-slit 3b, and the phase grating 5.

Figure 27:
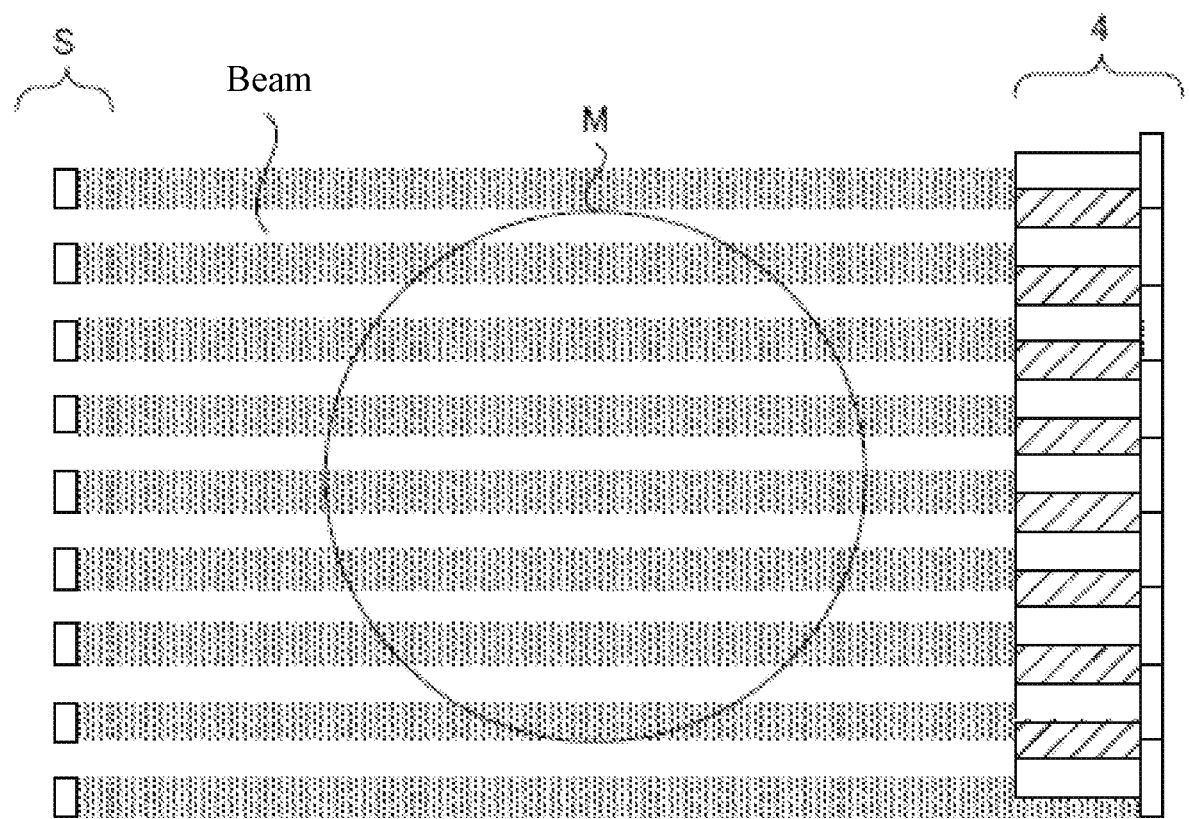
FIG. 27 is a schematic diagram explaining one modified Example according to the present invention.

With the configuration of FIG. 27, it is possible to perform the same imaging as in the above-described FIG. 24. That is, in the detection element 4p of FIG. 24, the portion where the absorption line 6a of the absorption grating 6 is provided corresponds to the portion where the glass element G of the alternative layer is provided in the detection element 4p of FIG. 27. In addition, in the detection element 4p of FIG. 24, the portion exposed from the absorption line 6a corresponds to the portion where the scintillator element C of the alternative layer is provided in the detection element 4p of FIG. 27. Therefore, by using the configuration of FIG. 27, it is possible to capture an interference image showing the degree to which the X-rays bend upward.

Figure 29:
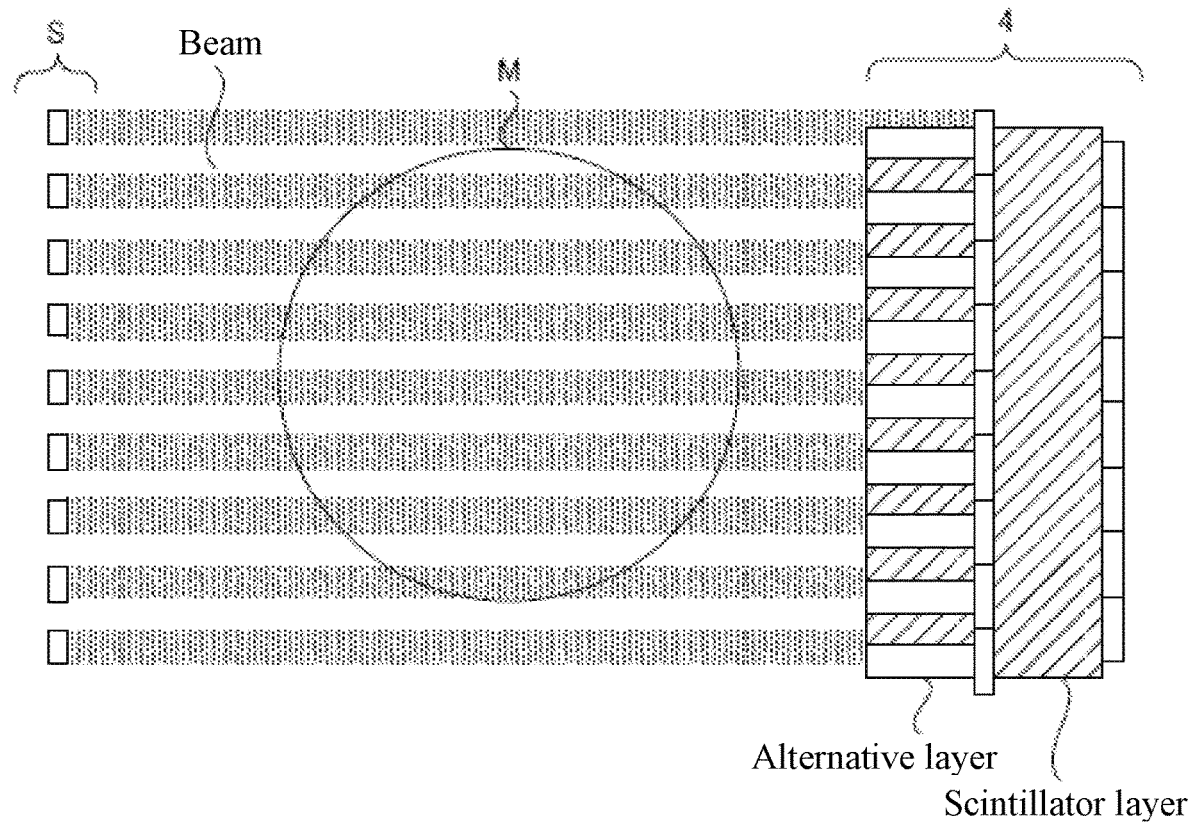
FIG. 29 is a schematic diagram explaining one modified Example according to the present invention.

(4) The present invention can also be applied to a configuration in which two interference images are captured at once, which further developed the above-described modified example (3). In the FPD 4 according to this modified example, as shown in FIG. 29, to the alternative layer and the two-dimensional matrix layer described in FIG. 26, a scintillator layer constituted only by a scintillator and another two-dimensional matrix layer are provided. The two-dimensional matrix layer sandwiching the scintillator layer is positioned so that the respective detection elements are located at a position displaced by half of the detection element. With this, the image capturing of the interference image according to FIG. 26 is performed by a two-dimensional matrix layer located on the left side of the scintillator layer, and the image capturing of the interference image according to FIG. 27 is performed by the two-dimensional matrix layer located on the right side of the scintillator layer. That is, according to this modified example, even without performing image capturing twice while changing the positional relationship between the stripe-shaped beam and the FPD 4, in a state in which the positional relationship between the strip-shaped beam and the FPD 4 is fixed, it is possible to capture two images, i.e., the interference image according to FIG. 26 (FIG. 22) and the interference image according to FIG. 27 (FIG. 24), with one X-ray irradiation.

Figure 30:
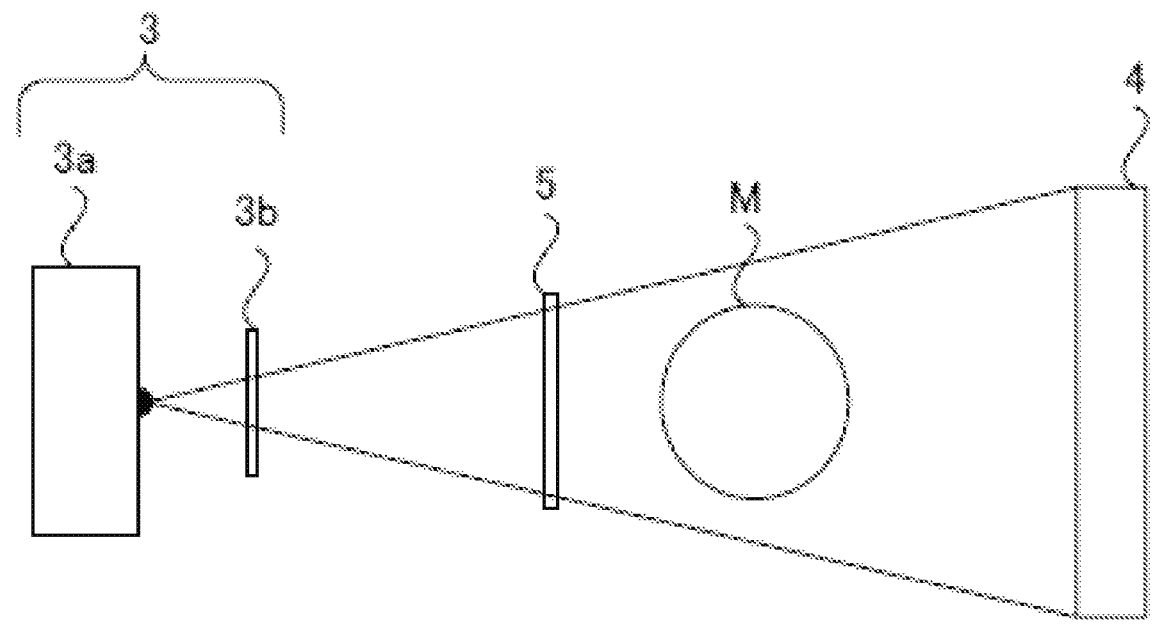
FIG. 30 is a schematic diagram explaining one modified Example according to the present invention.

(5) According to the configuration of Example 1, it is configured such that the absorption grating 6 moves with respect to the FPD 4, but the present invention is not limited to this configuration. As shown in FIG. 30, the present invention may be applied to an X-ray phase contrast imaging apparatus in which absorption grating 6 is omitted.

According to this modified example, there is no need to move the FPD 4. This is because the detection element 4p on the detection surface of the FPD 4 is fine enough to directly detect the self-image of the phase grating 5. According to this method, it is not necessary to generate a self-image based on a plurality of interference images as described in FIG. 7, and it is possible to acquire a self-image itself by one image capturing.

Figure 31:
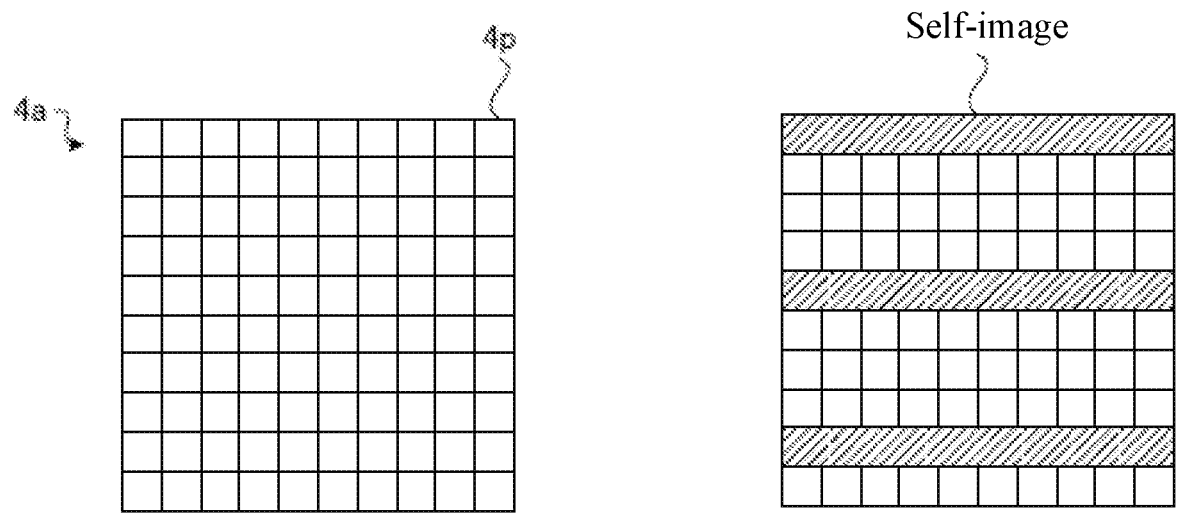
FIG. 31 is a schematic diagram explaining one modified Example according to the present invention.

On the detection surface of the FPD 4 according to the modified example, the detection elements 4p are arranged in a matrix as shown in FIG. 31. Since the detection element 4p is sufficiently fine, the width of the dark line of the self-image is about the same as the width of the detection element 4p. And the array pitch of the detection elements 4p of the detection surface is smaller than the array pitch of the image of the grating absorber at the detection surface.

Although not illustrated, the detection element 4p may be configured to be fine so that the width of the dark line of the self-image becomes wider than the width of the detection element 4p.

Figure 32:
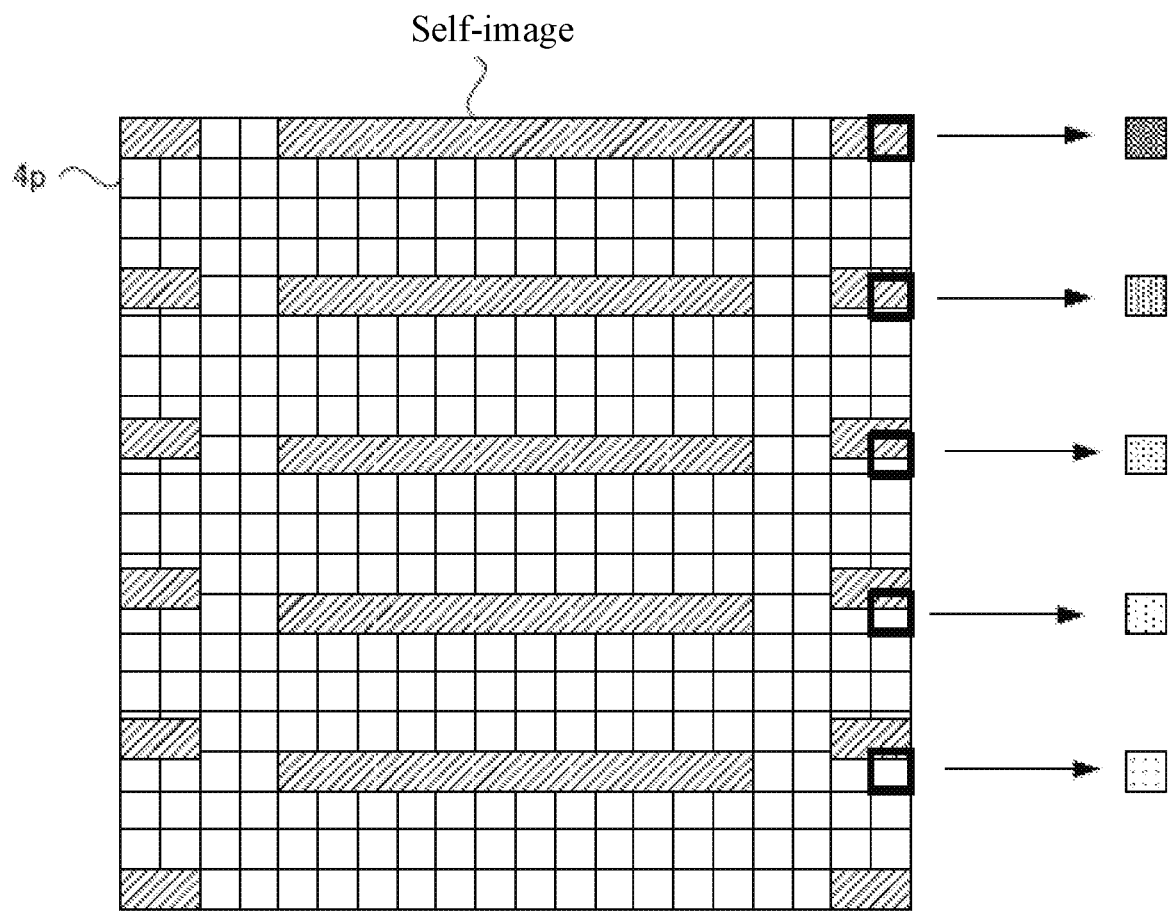
FIG. 32 is a schematic diagram for explaining one modified example according to the present invention.

FIG. 32 shows how the array of the detection elements 4p and the self-image of the phase grating 5 interfere at both end portions of the detection surface at the end of the FPD 4. In the center portion of the FPD 4, since the array pitch of the dark lines constituting the self-image is an integer multiple of the width of the detection element 4p, only the self-image is detected as it is on the detection surface. However, at both end portions of FPD 4, since the array pitch of the dark lines constituting the self-image is not an integer multiple of the width of the detection element 4p, in this portion, the detection element 4p array and the self-image of the phase grating 5 interfere.

This point will be described with reference to FIG. 32. At the upper end portion of the FPD 4 shown in FIG. 32, the dark line of the self-image just overlaps the detection element 4p. Focusing on the vertical row located at the right end of the detection element 4p, it is understood that the dark line of the self-image is superimposed every four. However, since the array pitch of the dark lines is not an integer multiple of the width of the detection element 4p, the dark line which just overlaps the detection element 4p on the upper side gradually shifts from the detection element 4p as it goes downward when looking in order of the detection element 4p apart from the detection element 4p by four (4), the detection element 4p apart from the detection element 4p by eight (8), and the detection element 4p apart from the detection element 4p by twelve (12).

The position calculation unit 11 according to this modified example calculates the relative position between the phase grating 5 and the FPD 4 based on the difference in the detected amount of X-rays that differs among the respective detection elements 4p located in the area where both end portions of the phase grating 5 on the detection surface appears. The position calculation unit 11 detects the moire (interference fringe) occurring between the image of the pattern of the reference area appeared on the detection surface and the pattern on the absorption grating and calculate the relative position between the phase grating 5 and the FPD 4. Further, at this time, the position calculation unit 11 also calculates the position of the X-ray source 3 with respect to the phase grating 5 and the FPD 4. This is because the way of appearing the interference fringe changes depends on the relative position of the three members, i.e., the X-ray source 3, the phase grating 5, and the FPD 4.

This misalignment between the detection element 4p and dark line can be observed by the change of the X-ray dose detected by the detection element 4p. That is, since the detection element 4p at the upper end position just overlap the dark line of the self-image, almost no X-ray is detected.

Looking at the output of the detection element 4p in order of a detection element away by four (4), the detection element 4p away from by eight (8), the detection element 4p away from twelve (12), and the detection element 4p away from by sixteen (16), the detection element gradually detects more X-rays. This is because overlapping of dark lines is gradually eliminated. From the difference in the detection amount of the X-rays, the relative position between the array of the detection element 4p and the self-image of the phase grating 5 can be calculated. The calculated relative position can be used to correct the captured self-image. That is, the captured self-image is disturbed by the fact that the relative position between the array of the detection element 4p and the self-image of the phase grating 5 is not ideal. If the relative position can be accurately measured, this disturbance can be removed by correction.

As described above, the present invention can also be applied to a device other than a device having the absorption grating 6. That is, in a detection surface, detection elements 4p each having a predetermined size are arranged in a matrix. Therefore, the FPD 4 discretely samples the X-rays to generate an interference image. Therefore, interference may occur between the array of the detection element 4p and the grating image on the detection surface. Based on this principle, an interference fringe is generated at the portion where the reference area of the phase grating 5 appears in the interference image output from the FPD 4. This interference fringe represents the relative position between the phase grating 5 and the FPD 4. Both end portions of the phase grating 5 are reflected in the captured interference image, and in the interference image, the center portion of the phase grating 5 is located at a different portion. For this reason, according to the present invention, there is no need to separately perform image capturing in the absence of the subject M to grasp the relative position between the phase grating 5 and the FPD 4. This is because in the interference image, an interference fringe representing the relative position between the grating image and the FPD 4 appears apart from the area in which the subject M appears.

(6) In the configuration of Example 1, the interference image is captured in one shot, but the present invention is not limited to this configuration. It is also possible to generate an interference image by consecutively capturing a plurality of images and adding them together.

Figure 33:
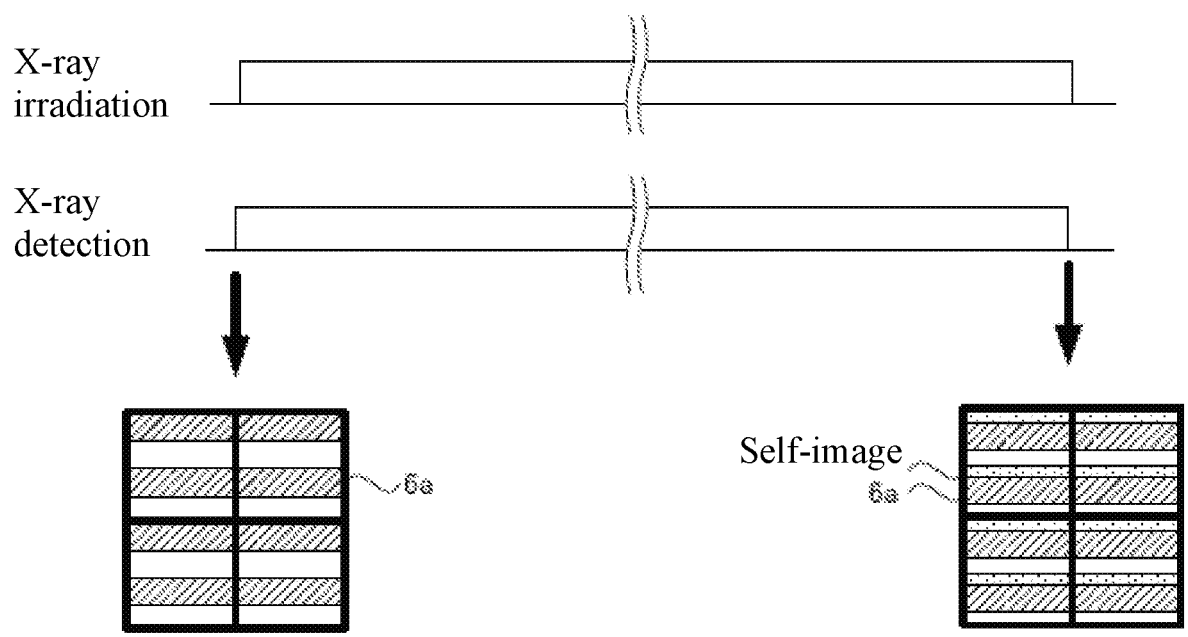
FIG. 33 is a schematic diagram explaining one modified Example according to the present invention.

FIG. 33 illustrates the imaging method of the interference image in Example 1. In the configuration of Example 1, it is configured such that an X-ray detection is continuously performed during one X-ray irradiation and the detection data accumulated in the FPD 4 is read after completion of the X-ray irradiation. In such an imaging method, only one image is obtained during one X-ray irradiation. Such an imaging method has the following problems. Due to the thermal expansion of the optical system, vibration, etc., during imaging, the position of the phase grating 5 shifts or the radiation generation point of the radiation source 3 deviates from the ideal position. Therefore, there is a possibility that errors occur. That is, as shown in FIG. 33, at the start of imaging, the absorption line 6a of the absorption grating 6 and the self-image of the phase grating 5 are just overlapped. As the X-ray irradiation is continuously performed, the relative position between the phase grating 5 and the absorption grating 6 gradually changes and the position of the absorption line 6a and the position of the self-image of the phase grating 5 also deviate accordingly. In the configuration of Example 1, this situation is not taken into consideration, and an interference image is generated assuming that the relative position of the phase grating 5 and the absorption grating 6 does not change from the start of imaging.

Figure 34:
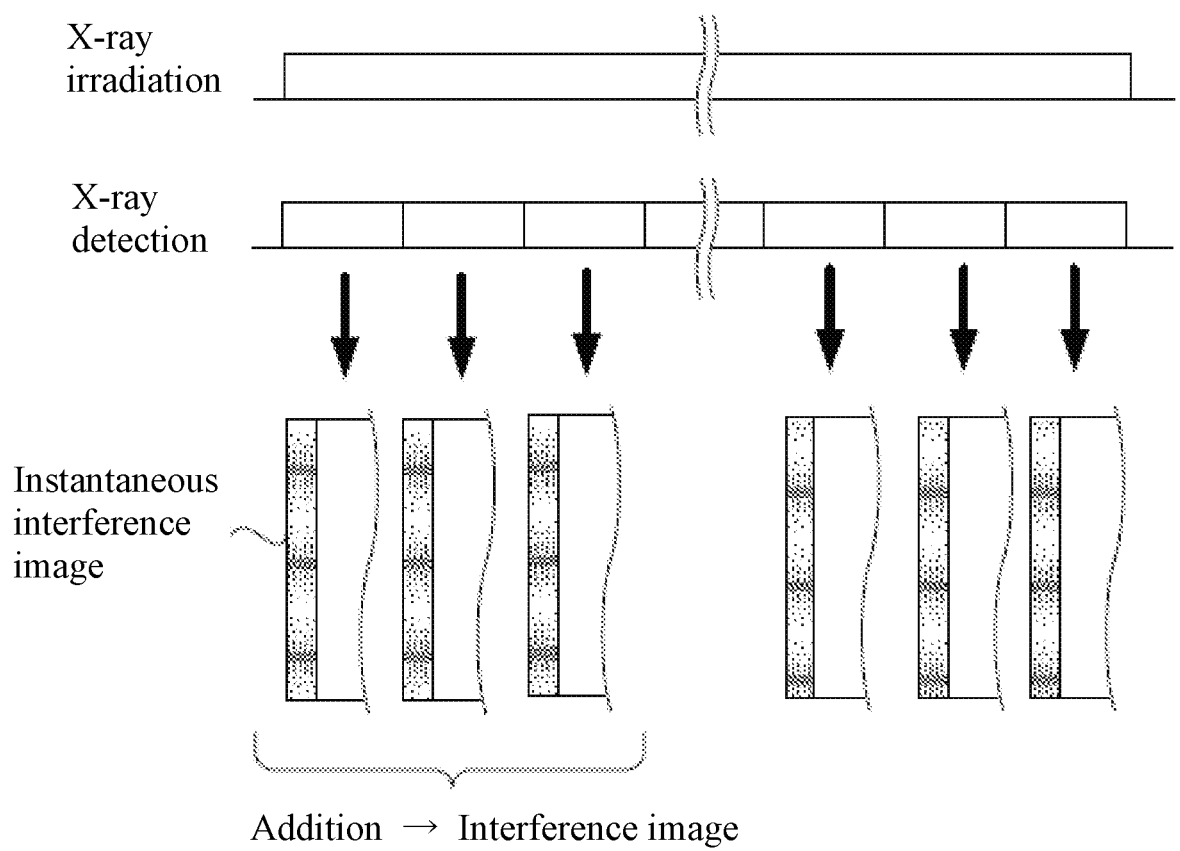
FIG. 34 is a schematic diagram explaining one modified Example according to the present invention.

FIG. 34 illustrates the configuration of this modified example. According to the modified example, the FPD 4 is read many times during one radiation imaging and a plurality of images is generated based on the result. The image generated at this time is an image in which the interference image is insufficiently exposed and it is called an instantaneous interference image. Let's focus on the end portion of the instantaneous interference image. At the end of the image, the interference fringe formed by the interference of the absorption grating 6 and the self-image of the phase grating 5 appears. As described with reference to the left side of FIG. 14, the interference fringe at the start of imaging represents that the absorption line 6a of the absorption grating 6 and the dark line of the self-image of the phase grating 5 are just overlapped. The interference fringe appeared at the end of the instantaneous interference image continuously captured while continuing imaging gradually changes. This is because that the relative position between the absorption grating 6 and the phase grating 5 changed due to the influence of the thermal expansion of the optical system during imaging. The interference image of this modified example is generated by adding only the instantaneous interference images captured when the relative position between the absorption grating 6 and the phase grating 5 in the consecutively captured instantaneous interference image has not changed from the start of imaging. By generating the interference image as described above, it is possible to generate an interference image captured with the positional relationship between the absorption grating 6 and the phase grating 5 certainly in a certain state. Further, when it is detected that the relative position has changed from the start of imaging, it is possible to perform long-time exposure imaging by continuously performing imaging by performing an operation of returning the relative position to the imaging start position without adding the changed instantaneous interference image.

Figure 35:
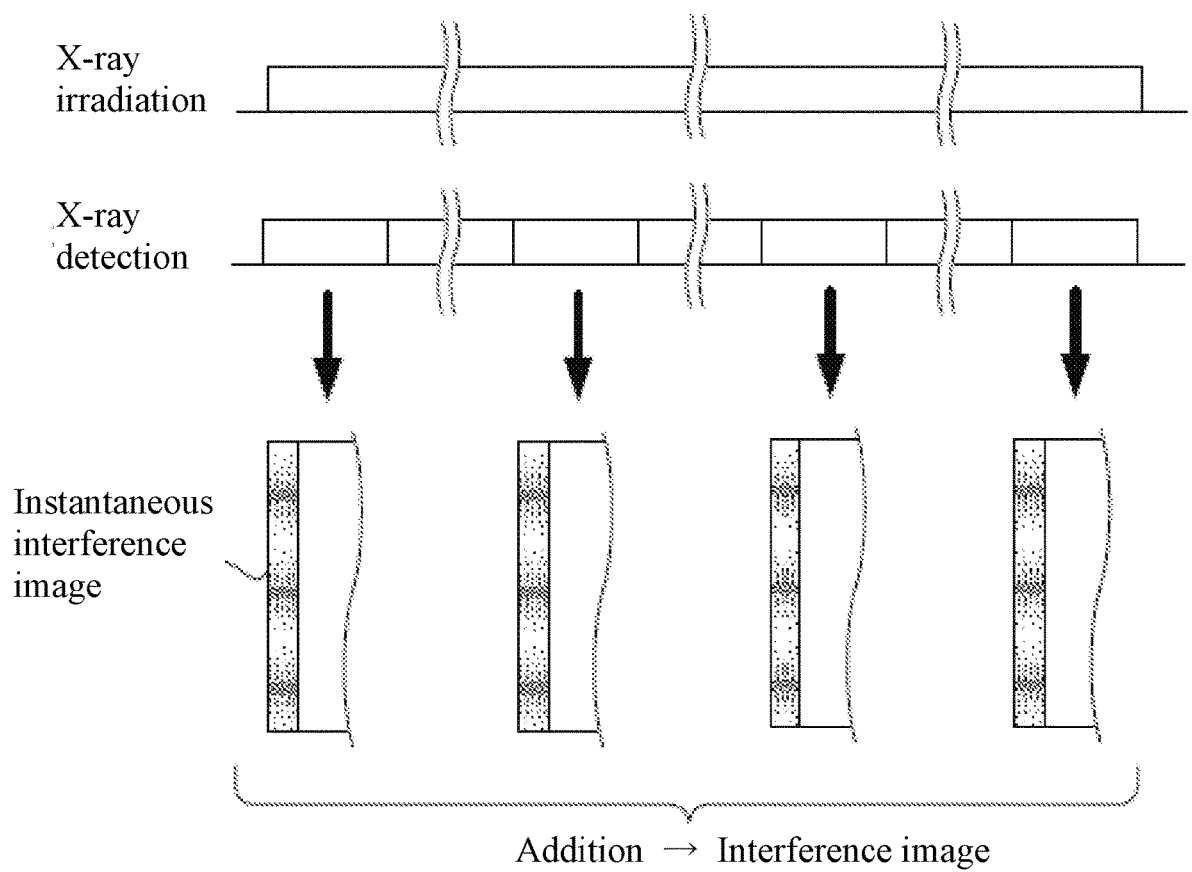
FIG. 35 is a schematic diagram for explaining one modified Example according to the present invention.

In FIG. 35, it is assumed that the optical system is vibrating. In this case, the interference fringe appeared at the end portion of the instantaneous interference image changes periodically. The interference image in this case is also generated by adding only the instantaneous interference images captured when the relative position between the absorption grating 6 and the phase grating 5 in the consecutively captured instantaneous interference image has not changed from the start of imaging. Therefore, the instantaneous interference image to be added becomes those captured at a certain time interval that is longer than the temporal interval necessary for image continuous capturing. Note that in this case, it is more preferable to determine the interval of the consecutive imaging in consideration of the natural frequency of the anti-vibration function.

This modified example can be applied not only to Example 1 but also to imaging of other modified examples.

(7) Although the patterns provided in the phase grating and the absorption grating in the present invention are in the form of stripes, the present invention is not limited to this configuration. The pattern may be other patterns such as, e.g., a checkered pattern.

DESCRIPTION OF REFERENCE SYMBOLS 3 radiation source
4 FPD (detection unit)
5 phase grating (grating)

6 absorption grating (filter)
11 position calculation unit
12 self-image generation unit grating image generation unit)
15 absorption grating moving mechanism (elative position changing unit)

The invention claimed is:

1. An X-ray phase contrast imaging apparatus comprising:
   an X-ray source configured to irradiate X-rays;
   a grating provided with a subject grating area which is an area provided with a predetermined pattern for absorbing the X-rays and through which an X-ray beam that passes through a subject passes and a reference grating area which is an area provided with a pattern different from the pattern of the subject grating area;
   (A) an absorption grating provided with a predetermined pattern for absorbing the X-rays;
   (B) a detector configured to detect an image of the grating on a detection surface in which detection elements for detecting the X-rays are arranged in a matrix;
   (C1) a position calculator configured to calculate a relative position of the X-ray source, the grating, and the absorption grating by detecting moire occurring between an image of the pattern of the reference grating area appearing on the detection surface and a pattern on the absorption grating; and
   an image generator configured to execute a correction by referring to the calculated relative position when generating an image based on an output of the detector.

2. The X-ray phase contrast imaging apparatus as recited in claim 1,
   wherein the reference grating area of the grating is provided at an end portion of the subject grating area in one direction.

3. The X-ray phase contrast imaging apparatus as recited in claim 2,
   wherein the reference grating area of the grating is provided at both end portions of the subject grating area in one direction.

4. The X-ray phase contrast imaging apparatus as recited in claim 1,
   wherein the pattern in the reference grating area is configured by arranging dark lines for absorbing X-rays,
   wherein the pattern in the absorption grating is configured by arranging dark lines for absorbing X-rays, and
   wherein an array pitch of the dark lines in the reference grating area is not an integer multiple of an array pitch of the dark lines in the absorption grating.

5. The X-ray phase contrast imaging apparatus as recited in claim 1,
   wherein the pattern in the subject grating area of the grating is for a moire single imaging method.

6. The X-ray phase contrast imaging apparatus as recited in claim 1,
   wherein a plurality of images are added based on the relative position calculated by the position calculator.

7. An X-ray phase contrast imaging apparatus comprising:
   an X-ray source configured to irradiate X-rays;
   a grating provided with a subject grating area which is an area provided with a predetermined pattern for absorbing the X-rays and through which an X-ray beam that passes through a subject passes and a reference grating area which is an area provided with a pattern different from the pattern of the subject grating area;
   (B) a detector configured to detect an image of the grating on a detection surface in which detection elements for detecting the X-rays are arranged in a matrix;
   (C2) a position calculator configured to calculate a relative position of the radiation X-ray source and the grating by detecting moire occurring between an image of the pattern of the reference grating area appearing on the detection surface and an array of each detection element; and
   an image generator configured to execute a correction by referring to the calculated relative position when generating an image based on an output of the detector.

8. The X-ray phase contrast imaging apparatus as recited in claim 7,
   wherein a pattern in the reference grating area is configured by arranging dark lines for absorbing X-rays, and an array pitch of the dark lines is not an integer multiple of an array pitch of the detection element.

9. The X-ray phase contrast imaging apparatus as recited in claim 7,
   wherein the reference grating area of the grating is provided at an end portion of the subject grating area in one direction.

10. The X-ray phase contrast imaging apparatus as recited in claim 7,
    wherein the pattern in the subject grating area of the grating is for a moire single imaging method.

11. The X-ray phase contrast imaging apparatus as recited in claim 7,
    wherein a plurality of images are added based on the relative position calculated by the position calculator.

* * * * *